(12) United States Patent
Hammer et al.

(10) Patent No.: US 7,491,866 B2
(45) Date of Patent: Feb. 17, 2009

(54) TRANSGENIC RATS AND SPERMATOGONIAL STEM CELLS

(75) Inventors: Robert E. Hammer, Dallas, TX (US); Franklin Kent Hamra, Keller, TX (US); Jennifer T. Cronkhite, Dallas, TX (US)

(73) Assignee: Board of Regents University of Texas System, Austin, TX (US)

( * ) Notice: Subject to any disclaimer, the term of this patent is extended or adjusted under 35 U.S.C. 154(b) by 0 days.

(21) Appl. No.: 11/557,434

(22) Filed: Nov. 7, 2006

(65) Prior Publication Data

US 2007/0136830 A1 Jun. 14, 2007

Related U.S. Application Data

(60) Provisional application No. 60/771,875, filed on Feb. 10, 2006, provisional application No. 60/734,754, filed on Nov. 9, 2005.

(51) Int. Cl.
*A01K 67/00* (2006.01)
*A01K 67/033* (2006.01)

(52) U.S. Cl. .......................... 800/13; 435/325; 435/455

(58) Field of Classification Search .................... 800/13; 435/325, 455
See application file for complete search history.

(56) References Cited

OTHER PUBLICATIONS

Cronkhite (Dev. Biol., Aug. 1, 2005, vol. 284, p. 171-183).*
BioTech Dictionary definition of "germ cell".*
Hamra (Developmental Biology, May, 15, 2004, vol. 269, No. 2, p. 393-410).*
Hamra (PNAS, Nov. 29, 2005, vol. 102, No. 48, p. 17430-17435).*
Ryu (PNAS, Oct. 4, 2005, vol. 102, No. 40, p. 14302-14307).*
Chiquoine, A. D. (1954). The identification, origin, and migration of the primordial germ cells in the mouse embryo. Anat Rec 118, 135-146.
Ginsburg, M., Snow, M. H., and McLaren, A. (1990). Primordial germ cells in the mouse embryo during gastrulation. Development 110, 521-528.
Okazawa, H., Okamoto, K., Ishino, F., Ishino-Kaneko, T., Takeda, S., Toyoda, Y., Muramatsu, M., and Hamada, H. (1991). The oct3 gene, a gene for an embryonic transcription factor, is controlled by a retinoic acid repressible enhancer. Embo J 10, 2997-3005.
Yoshimizu, T., Sugiyama, N., De Felice, M., Yeom, Y. I., Ohbo, K., Masuko, K., Obinata, M., Abe, K., Scholer, H. R., and Matsui, Y. (1999). Germline-specific expression of the Oct-4/green fluorescent protein (GFP) transgene in mice. Dev Growth Differ 41, 675-684.
Fox, N., Damjanov, I., Martinez-Hernandez, A., Knowles, B. B., and Solter, D. (1981). Immunohistochemical localization of the early embryonic antigen (SSEA-1) in postimplantation mouse embryos and fetal and adult tissues. Dev Biol 83, 391-398.
Lange, U. C., Saitou, M., Western, P. S., Barton, S. C., and Surani, M. A. (2003). The fragilis interferon-inducible gene family of transmembrane proteins is associated with germ cell specification in mice. BMC Dev Biol 3, 1-11.
Chambers, I., Colby, D., Robertson, M., Nichols, J., Lee, S., Tweedie, S., and Smith, A. (2003). Functional expression cloning of Nanog, a pluripotency sustaining factor in embryonic stem cells. Cell 113, 643-655.
Tsuda, M., Sasaoka, Y., Kiso, M., Abe, K., Haraguchi, S., Kobayashi, S., and Saga, Y. (2003). Conserved role of nanos proteins in germ cell development. Science 301, 1239-1241.
Tanaka, S. S., Toyooka, Y., Akasu, R., Katoh-Fukui, Y., Nakahara, Y., Suzuki, R., Yokoyama, M., and Noce, T. (2000). The mouse homolog of Drosophila Vasa is required for the development of male germ cells. Genes Dev 14, 841-853.
Enders, G. C., and May, J. J., 2nd. (1994). Developmentally regulated expression of a mouse germ cell nuclear antigen examined from embryonic day 11 to adult in male and female mice. Dev Biol 163, 331-340.
Gill, T. J., 3rd, Smith, G. J., Wissler, R. W. & Kunz, H. W. The Rat as an Experimental Animal. (1989) Science 245, 269-276.
Abbott, A., The Renaissance rat. (2004) Nature 428, 464-466.
Zambrowicz, B. P., Imamoto, A., Fiering, S., Herzenberg, L. A., Kerr, W. G., and Soriano, P. (1997). Disruption of overlapping transcripts in the ROSA beta geo 26 gene trap strain leads to widespread expression of beta-galactosidase in mouse embryos and hematopoietic cells. Proc Natl Acad Sci U S A 94, 3789-3794.
Kisseberth, W. C., Brettingen, N. T., Lohse, J. K., and Sandgren, E. P. (1999). Ubiquitous expression of marker transgenes in mice and rats. Dev Biol 214, 128-38.
Young, S., Aldons, JL., Hammer, RE. (1999). Molecular Basis of Cardiovascular Disease. In "Genetically Modified Animal Models in Cardiovascular Research" (K. Chien, Ed.), pp. 37-85. W. B. Saunders Company, Philadelphia.
MacLean-Hunter, S., Evans, M. (1999). Non-Surgical Method for the Induction of Delayed Implantation and Recovery of Viable Blastoysts in Rats and Mice by the Use of Tamoxifen and Depo-Provera. Molecular Reproduction and Development 52, 29-32.
Hogan, B., Beddington, R, Constantini, F, and Lacy, E. (1994). "Manipulating the mouse embryo: A laboratory manual." Cold Spring Harbor Laboratory Press, Plainview, NY.
Islam, M. Q., and Levan, G. (1987). A new fixation procedure for quality G-bands in routine cytogenetic work. Hereditas 107, 127-130.
Behboudi, A., Roshani, L., Kost-Alimova, M., Sjostrand, E., Montelius-Alatalo, K., Rohme, D., Klinga-Levan, K., and Stahl, F. (2002). Detailed chromosomal and radiation hybrid mapping in the proximal part of rat Chromosome 10 and gene order comparison with mouse and human. Mamm Genome 13, 302-309.
Helou, K., Yan, Q., Yuan, X. J., Kunz, H. W., Levan, G., and Gill, T. J., 3rd. (1999). Cytogenetic localization of the growth and reproduction complex (Grc) in the rat and in the mouse and its position in relation to RT1.EC and other loci in the rat MHC. Hereditas 130, 105-109.
Palmiter, R. D., and Brinster, R. L. (1986). Germ-line transformation of mice. Annu Rev Genet 20, 465-499.
Zernicka-Goetz, M. (1994). Activation of embryonic genes during preimplantation rat development. Mol Reprod Dev 38, 30-35.

(Continued)

*Primary Examiner*—Michael C. Wilson
(74) *Attorney, Agent, or Firm*—Stephen A. Bent; Foley & Lardner LLP

(57) ABSTRACT

A transgenic rat expresses a gene of interest, such as EGFP, exclusively in the germ cells of both males and females. From such a transgenic rat one can isolate a line of spermatogonial stem cells, which can renew and proliferate in culture.

4 Claims, 15 Drawing Sheets

OTHER PUBLICATIONS

Hamra, F., Schultz, N., Chapman, K. M., Grellhesl, D. M., Cronkhite, J. T., Hammer, R. E., and Garbers, D. L. (2004). Defining the spermatogonial stem cell. Dev Biol 269, 393-410.

Hamra, F. K., Gatlin, J., Chapman, K. M., Grellhesl, D. M., Garcia. J. V., Hammer, R. E., and Garbers, D. L. (2002). Production of transgenic rats by lentiviral transduction of male germ-line stem cells. Proc Natl Acad Sci U S A 99, 14931-14936.

Ogawa, T., Arechaga, J. M., Avarbock, M. R., and Brinster, R. L. (1997). Transplantation of testis germinal cells into mouse seminiferous tubules. Int J Dev Biol 41, 111-122.

Brinster, R. L., and Zimmermann, J. W. (1994). Spermatogenesis following male germ-cell transplantation. Proc Natl Acad Sci U S A 91, 11298-11302.

Dobrinski, I., Avarbock, M. R., and Brinster, R. L. (2000). Germ cell transplantation from large domestic animals into mouse testes. Mol Reprod Dev 57, 270-279.

Nagano, M., and Brinster, R. L. (1998). Spermatogonial transplantation and reconstitution of donor cell spermatogenesis in recipient mice. Apmis 106, 47-55; discussion 56-7.

Schultz, N., Hamra, F. K. & Garbers, D. L. A multiple of genes expressed solely in meiotic or postmeiotic spermatogenic cells offers a myriad of contraceptive targets. (2003) Proc Natl Acad Sci U S A 100, 12201-12206.

Heid, C. A., Stevens, J., Livak, K. J. & Williams, P. M. Real Time Quantitative PCR. (1996) Genome Res 6, 986-94.

Gibson, U. E., Heid, C. A. & Williams, P. M. A Novel Method for Real time Quantitative RT-PCR. (1996) Genome Res 6, 995-1001.

Mather, J. P., Saez. J. M. & Haour, F. Primary Cultures of Leydig Cells From Rat Mouse and Pig: Advantages of Porcine Cells for the Study of Gonadotropin Regulation of Leydig Cell Function. (1981) Steroids 38, 35-44.

Kanatsu-Shinohara, M., Ogonuki, N., Inoue, K., Miki, H., Ogura, A., Toyokuni, S. & Shinohara, T. Long-Term Proliferation in Culture and Germline Transmission of Mouse Male Germline Stem Cells. (2003) Biol Reprod 69, 612-616.

Ogawa, T. Dobrinski, I. & Brinster, R. L. Recipient preparation is critical for spermatogonial transplantation in the rat. (1999) Tissue Cell 31, 461-472.

McMahon, A. P. & Bradley, A. The Wnt-1 (int-1) Proto-Oncogene is Required for Development of a Large Region of the Mouse Brain (1990) Cell 62, 1073-1085.

McGuinness, M. P., Linder, C. C., Morales, C. R., Heckert, L. L., Pikus, J. & Griswold, M. D. Relationship of a Mouse Sertoli Cell Line (MSC-1) to Normal Sertoli Cells. (1994) Biol Reprod 51, 116-124.

Malkov, M., Fisher, Y. & Don, J. Developmental Schedule of the Postnatal Rat Testis Determined by Flow Cytometry (1998) Biol Reprod 59, 84-92.

Kubota, H., Avarbock, M. R. & Brinster, R. L. Growth factors essential for self renewal and expansion of mouse spermatogonial stem cells. (2004) Proc Natl Acad Sci U S A 101, 16489-16494.

Cheah, S. S. & Behringer, R. R. Contemporary Gene Targeting Strategies for the Novice. (2001) Mol Biotechnol 19, 297-304.

Te Riele, H., Maandag, E. R. & Berns, A. Highly efficient gene targeting in embryonic stem cells through homologous recombination with isogenic DNA constructs. (1992) Proc Natl Acad Sci U S A 89, 5128-5132.

F. Kent Hamra et al., "Self renewal, expansion and transfection of rat spermatogonial stem cells in culture", PNAS, vol. 102, No. 48, Nov. 29, 2005, pp. 17430-17435.

Jennifer T. Cronkhite et al., "Male and female germline specific expression of an EGFP reporter gene in a unique strain of transgenic rats", Development Biology 284 (2005) 171-183.

* cited by examiner

A. Homozygous Female X WT Male

B. WT Female X Homozygous Male

C. WT Female X WT Male

D. WT Female X Homozygous Male

SEQUENCE LISTING

<160> NUMBER OF SEQ ID NOS: 26

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aacttcaggg tcagcttgc                                              19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggtgttctgc tggtagtggt c                                           21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggcacaagc tggagtacaa c                                           21

<210> SEQ ID NO 4
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 4
tctgcttgtc ggccatgata                                                  20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aagtccctgc cctttgtaca ca                                               22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcctcactaa accatccaat cg                                               22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttgatccag gctaccaacg a                                                21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcccgctcaa agagggtatc                                                  20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgaccgcgg caattacac                                                   19

<210> SEQ ID NO 10
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 10
tgtacgtctg ccggatgct                                                19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcgggtagca cacacctctg t                                             21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaggcaccag cgagaccat                                                19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tggcacacct ctgctctatg                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tagacgccat agagatactg                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tagagaacgt ggagcaagtc                                               20

<210> SEQ ID NO 16
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 16
tcgaactgat gcccacttaa c                                              21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agttcgggtc cggaatgtg                                                 19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
accggtcaat gcttatgac                                                 19

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
accaactgcc tggagctctc t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
acctgctcca tgaaggttag c                                              21

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acccggtgca gtcattgag                                                 19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic

```
                                    -continued
      primer

<400> SEQUENCE: 22
gcagaatggt gccgatgtc                                                    19

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agggcagcaa catttttgaa a                                                 21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcgaagagga tgcccactac                                                   20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgcagatgac tgtggatcac c                                                 21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tcagataacg ggcaacttca g                                                 21
```

TRANSGENIC RATS AND SPERMATOGONIAL STEM CELLS

STATEMENT AS TO THE RIGHTS TO INVENTIONS MADE UNDER FEDERALLY SPONSORED RESEARCH AND DEVELOPMENT

The present invention was made with U.S. government support under Training Grant No. T32-GM07062-29, awarded by the National Institutes of Health. The government has certain rights in this invention.

BACKGROUND OF THE INVENTION

The present invention relates to ongoing efforts to produce rat genetic models through gene targeting technology. More particularly, the invention relates to a transgenic line of rats that express a gene of interest, e.g., enhanced green fluorescent protein (EGFP), exclusively in the germ-line, and to genetically modified spermatogonial stem cells obtained from these transgenic rats.

Germ cells have the ability to transmit genetic information from one generation to the next. Currently, there are no known markers for germ cells that are either expressed throughout germ cell development or that are exclusive to the germ cells.

The precursors to germ cells, primordial germ cells (PGCs), have been shown to contain high alkaline phosphatase activity (AP). Other molecules, such as oct3/4, stage specific embryonic antigen 1 (SSEA1), fragillis, nanog, nanos, vasa and germ cell nuclear antigen (GCNA), also have been suggested as reliable molecular markers for identifying developing germ cells (Ref. 1-10). Yet AP, oct3/4, SSEA1, nanog, and fragillis are expressed as well in undifferentiated cells of the early mammalian embryo (blastocyst to epiblast in the mouse); hence, they do not distinguish emerging germ cells from other undifferentiated cells of the embryo. Markers such as vasa and GCNA are germ cell-specific but are not expressed during all stages of germ cell development and GCNA is sex-specific. Thus, a single molecule has not been reported in mammals that marks the germ cell lineage throughout development.

The laboratory rat represents one of the most comprehensively studied mammalian species, with described use in more than a million publications in a wide range of medically relevant areas. Qualities such as size, fecundity, behavior, ease of surgical techniques, tissue sampling and general laboratory management have contributed to its popularity (Refs. 11-13). The rat is a much better animal model than the mouse to study human physiology and disease. However, failures in culturing pluripotent ES cells from the rat has resulted in the mouse becoming a widely popular animal model, because mouse embryonic stem (ES) cells can renew with a sense of immortality. An alternative to ES cells in rat model would be spermatogonial stem cells. In the past, however, rat spermatogonia could not be propagated in culture and had to be isolated fresh from rats for experimentation.

SUMMARY OF THE INVENTION

To address the aforementioned needs, the present invention provides, in one aspect, a transgenic rat that expresses a gene of interest exclusively in the germ cell lineage of both males and females. As exemplified below, the gene of interest is an EGFP reporter transgene. The unique germ cell-specific expression pattern of transgenes in these rats (GCS-EGFP rats) indicates that the transgene locus is a molecular marker of the germline lineage in both sexes. Indeed, the EGFP-marked locus of GCS-EGFP rats is the first identified molecular marker of the germline lineage in both sexes of a mammal.

Accordingly, rats of the present invention constitute a powerful tool to address important questions in the germ cell field. Novel genes now can be identified and then, along with known genes, can be studied to understand their involvement in the delineation of the germline during development.

Because EGFP is a vital marker, germ cells at all stages of embryonic development can be isolated by FACS, and the RNA can be analyzed, e.g., using microarrays, to develop markers for distinct stages of germ cell development. Such genetic markers can be studied to determine their function during germ cell development and may lead to an understanding of the signaling pathways that govern that complex process. GCS-EGFP rats may also allow the identification of markers of the germ lineage at the earliest embryonic stages. Finally, the GCS-EGFP rats can be used to determine when PGCs first acquire stem cell activity. Purified populations of PGCs can be collected at different developmental stages and then assayed for stem cell activity by transplanting them to a recipient testis.

In a related aspect, the invention provides rat spermatogonial stem cells that encode a gene of interest capable of being expressed exclusively in the germ cell lineage of both males and females. Such spermatogonial stem cells can be generated from GCS-EGFP rats and vice versa. Spermatogonial stem cells of the invention can renew and proliferate in culture, some with a doubling time between 3-4 days. Spermatogonial stem cell lines can be isolated and cryopreserved and, upon subsequent thawing, continue to self-renew. In one embodiment, self-renewable G418-resistant cell lines can be obtained by transfecting the spermatogonial stem cells with a plasmid containing the neomycin phosphotransferase (neo) selectable marker.

The invention further provides a method of propagating rat spermatogonial stem cells in culture, comprising (i) culturing spermatogonial stem cells on gelatin in S-medium, (ii) collecting spermatogonial stem cells and passaging them onto monolayers of MEFs in SA-medium, and, optionally, (iii) maintaining spermatogonial stem cells in SA medium containing GFRα1.

DETAILED DESCRIPTION OF THE PREFERRED EMBODIMENTS

Figure 1:
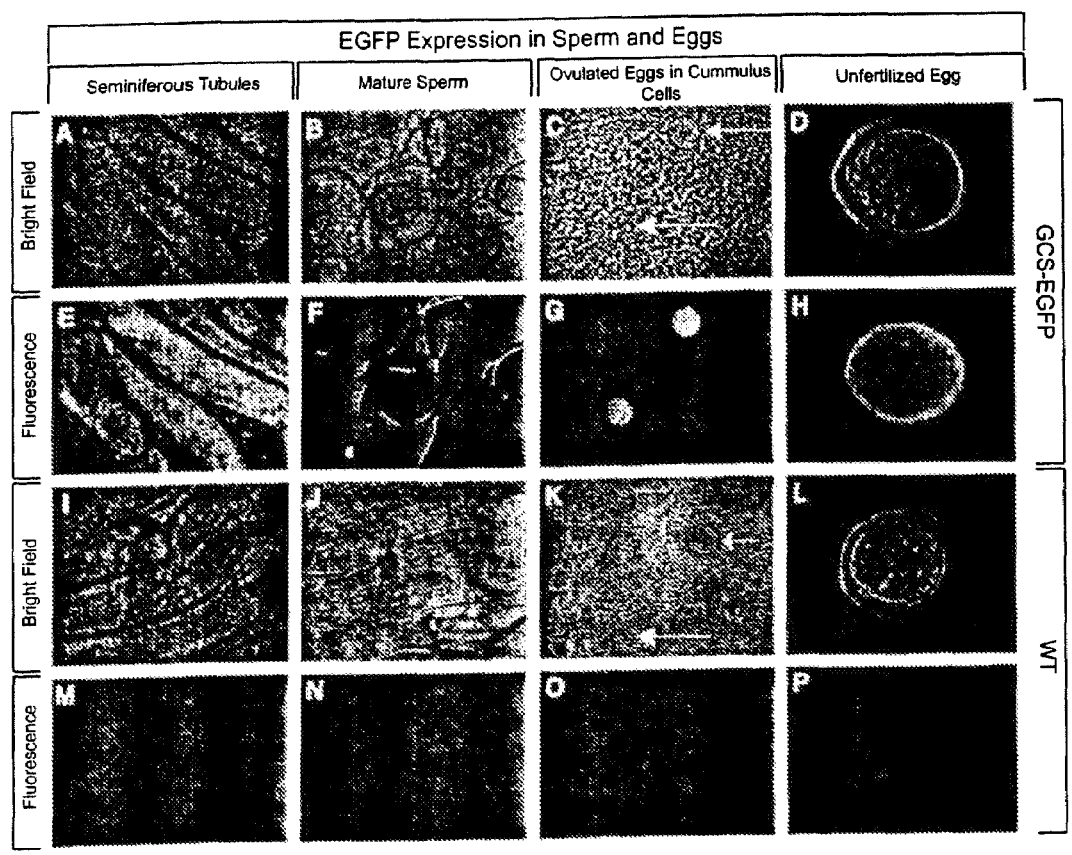
FIG. 1 shows that the EGFP is expressed in spermatozoa and eggs in GCS-EGFP rats. (A-H) Germ cells from GCS-EGFP rats; (A-D) DIC photomicrographs and (E-H) fluorescent photomicrographs of the same specimens as in panels (A-D). (A, E) Isolated seminiferous tubules dissected from the testis, (B, F) cauda epididymal sperm cells, (C, G) unfertilized eggs in the associated cumulus masses, and (D, H) a denuded unfertilized, metaphase-II egg. (I-P) Germ cells from WT Sprague-Dawley rats; (I-L) DIC photomicrographs and (M-P) fluorescent photomicrograph of the same specimens in panel (I-L). (H and P) Eggs were counterstained with HZoechst 33442 to visualize DNA (blue).

One aspect of the present invention relates to a transgenic rat, which expresses a gene of interest exclusively in the germ cells of both males and females. As exemplified herein, the gene of interest is a reporter gene that encodes enhanced green fluorescent protein (EGFP). Some exemplary utilities of the transgenic rats are as a tool to study germ cell origin, development, and differentiation, and to assess the plasticity of adult somatic stem cells to become male germ cells. The chromosomal location of the transgene has been determined to be on chromosome 11 in the q11-q12 region, proximal to the Mx1, Kcnj6, Ncam2, and Grik1 genes. This region is syntenic to mouse chromosome 16 and human chromosome 21. It is known that this region encompasses the Down syndrome critical region genes 1-6.

In another aspect, the present invention concerns rat spermatogonial stem cells that contain a gene of interest that is expressed exclusively in the germ cell lineage of both males and females. Such spermatogonial stem cells can be produced from the above-described transgenic rats and can renew and proliferate in culture for many passages. These cell lines can be isolated and cryopreserved and, upon subsequent thawing, continue to self-renew. GCS-EGFP spermatogonial stem cells, described herein, are deposited at the American Type Culture Collection Patent Depository, pursuant to 37 C.F.R. §§ 1.801-1.809. The deposit number is PTA-7214. Because the spermatogonial stem cells can be used to generate the transgenic rats described herein and vice versa, the cells being deposited constitute not only a source of spermatogonial stem cells but also of transgenic rats.

Cell lines of the invention can be genetically modified further in vitro, in much the same manner as seen with mouse ES cells. This alternative to the use of genetically modified ES cells can result in direct germ line transfer and an escape from the intervening formation of a mosaic animal.

In one embodiment, self-renewable G418-resistant cell lines can be obtained by transfecting spermatogonial stem cells with a plasmid containing the neomycin phosphotransferase (neo) selectable marker. Transfer of this technology to other animals, including human, may result in the correction of certain forms of male infertility, the preservation of an individual's germ-line, and the potential use of these cells for the generation of pluripotent stem cells, which would eliminate a need to use ES cells to derive specialized cell types.

In another embodiment, the invention provides a method for propagating spermatogonial stem cells in culture, comprising the steps of (i) culturing spermatogonial stem cells on gelatin in S-medium, (ii) collecting spermatogonial stem cells and passaging them onto monolayers of MEFs in SA-medium, and, optionally, (iii) maintaining spermatogonial stem cells in SA medium containing GFRα1. Propagating spermatogonial stem cells in culture eliminates the need to isolate spermatononia from rats for each experiment. The spermatogonial lines can be used as vectors for germline transmission of natural or genetically modified rat genomes, which allows for preservation of existing rat lines and the production of new transgenic rat lines, respectively. The spermatogonial lines also can be used in vitro and in vivo in models for studying spermatogenesis, and to screen for and identify molecules or drugs that regulate fertility in males (e.g., male contraceptives). Additionally, these cells are potentially a valuable source of pluripotent stem cells that can be used in rat models for human disease. A person skilled in the art can apply this technology to derive spermatogonial stem cell lines from other species than rats, which are illustrated in the present invention. This approach also could be applied to other types of male germ cells (spermatocytes, spermatids, spermatozoa) that can not be expanded in number in culture. These cells now could be derived in culture from the spermatogonial stem cells.

The detailed description of the present invention is provide below by the following examples, which are illustrative only and not limiting of the invention.

EXAMPLE 1

Generation and Characterization of ROSA-EGFP Transgenic Rat Lines

A. Construction of ROSA-EGFP Transgene and Production of Transgenic Rats.

A 0.8 Kb SalI-BamHI ROSA26 fragment (Ref. 14) was inserted between the SalI and BamHI restriction sites of the EGFP-N1 plasmid from Clontech to generate the ROSA-EGFP transgene (Ref. 14-15). The 1.8Kb SalI and AlfII ROSA-EGFP fragment was separated from vector DNA by gel electrophoresis and the fragment was isolated from the gel by perchlorate elution. Transgenic rats were produced by microinjection of the 1.8 kb ROSA-EGFP fragment into the pronucleus of Sprague Dawley rat eggs as described (Ref. 16); 6 transgenic rats were produced. Founders were mated with Sprague Dawley wild-type (WT) rats and 4 independent lines were established. Genotyping of founders was by dot blot analysis and progeny by either dot blot or PCR analysis of genomic DNA isolated from tail biopsies. PCR was performed using the forward primer EGFP5-1 (5'AACT-TCAGGGTCAGCTTGC) (SEQ ID NO: 1) and the reverse primer EGFP3-1 (5'GGTGTTCTGCTGGTAGTGGTC) (SEQ ID NO: 2) corresponding to nucleotides 971 to 1492 of the ROSA-EGFP DNA fragment that amplified a DNA product of 521 bp. Unless otherwise specified homozygous transgenic rats and WT Sprague Dawley rats were used for all described experiments. Animals were housed in SPF condition cages with a 12-hour light and 12-hour dark cycle and fed Teklad Mouse/Rat Diet (Harlan Teklad, Madison, Wis.) ad libitum.

B. Imaging of EGFP Fluorescence in Embryos.

Prepubertal female rats were superovulated by a standard regimen (Ref. 16) and placed overnight with stud males. The presence of sperm in the vaginal lavage or a copulatory plug the following morning indicated mating had occurred and was scored as day E0.5. Pre-implantation embryos were collected on the specified day of development in R1ECM medium (Specialty Media, Phillipsburg, N.J.), washed in R1ECM and held in R1ECM drop cultures overlaid with oil until use. Blastocyst implantation was delayed as previously described (Ref. 17). Briefly, WT females were mated with GCS-EGFP homozygous males and the morning of finding a copulatory plug was designated as E0.5. On E4.5, 50 µg tamoxifen (Sigma-Aldrich, St. Louis, Mo.) in an aqueous solution of corn oil was injected intraperitoneally and 5 mg Depo-Provera (Upjohn Co., Kalamazoo, Mich.) was injected subcutaneously. Delayed blastocysts were collected on E8.5 in R1ECM, washed in R1ECM and held in drop cultures in R1ECM until use. Epiblasts were dissected on day E8.5 and held in PBS until use. The genital ridge was dissected from E12.5 and E15.5 embryos in PBS, and gonads were dissected from E19.5 embryos in PBS. Embryos and epiblasts were visualized with a Nikon Eclipse TE2000-U inverted microscope using an EGFP filter. The genital ridges and embryonic gonads were visualized with a Nikon SMZ1500 stereoscope using an EGFP filter.

C. Imaging of EGFP Fluorescence in Adult Tissues.

Tissues were either directly visualized for EGFP expression using a Nikon SMZ1500 stereoscope or fixed in 4% paraformaldehyde overnight at 4° C., washed in PBS, placed in 30% sucrose overnight at 4° C. to equilibrate, embedded in freezing medium Tissue Tek OCT (optimal cutting temperature) (Sakura Finetek U.S.A., Inc. Torrance, Calif.) and frozen in a biocooler Histobath 2 (Shandon Lipshaw, USA) containing isopentane at −55° C. Frozen tissues were then sectioned at 10-12 µm on a Leitz cryostat and mounted on positively charged glass slides; Fisherbrand Superfrost Plus Slides (Fisher Scientific Co., Pittsburgh, Pa.), rehydrated with PBS, and immediately visualized for EGFP expression using an inverted Olympus IX70 microscope (Olympus Inc. Melville, N.Y.).

D. Imaging of EGFP Fluorescence in Mature Sperm.

Mature spermatozoa were collected from the cauda epididymis of WT and homozygous GCS-EGFP male rats that had mated with a female within the previous 7-10 days. The cauda epididymis was placed into one ml of a fertilization medium (Brinster medium for oocyte culture with 30 mg/ml of BSA) under oil and the body of the cauda epididymis was cut and gently squeezed to express the sperm cells. The spermatozoa were allowed to disperse by swim out for one hour during incubation at 37° C. in 5% $CO_2$ atmosphere. An aliquot of the sperm preparation was then placed directly on to a glass slide and viewed using Leica TCS SP2 AOBS: confocal microscope (Leica Microsystems, Wetzlar, Germany).

E. Alkaline Phosphatase Staining.

Epiblasts from E8.5 and genital ridges from E12.5 embryos were isolated by microdissection and fixed in 4% paraformaldehyde for 2 h at 4° C. The tissues were washed three times in PBS, incubated for one hour in 70% ethanol, and washed three times in distilled water. Tissues were stained with α-naphthyl phosphate/fast red TR (Sigma-Aldrich. St. Louis, Mo.) for 15 min at room temperature (Ref. 2), mounted on slides, overlaid with 70% glycerol and viewed on a Nikon Eclipse TE2000-U inverted microscope.

F. Quantitative Real-Time PCR.

Total cellular RNA was isolated from multiple organs of WT rats, homozygous GCS-EGFP rats, and line 7-10 rats using RNA Stat-60 (Tel-Test, Friendswood Tex.). One microgram of total RNA was reverse transcribed using random primers and Superscript III reagents (Invitrogen, Carlsbad, Calif.). Samples were diluted 1:10 and 3 µl were used for the PCR reaction. The PCR was performed using the SYBR Green PCR Master Mix (Applied Biosystems, Foster City, Calif.) and EGFP primers: forward EGFP2-5(5'GGGCA-CAAGCTGGAGTACAAC) (SEQ ID NO: 3) and reverse EGFP2-3(5'TCTGCTTGTCGGCCATGATA) (SEQ ID NO: 4), which were designed in Primer Express Ver. 2.0. Real-time PCR analysis was performed with the ABI PRISM 7900HT Sequence Detection System (Applied Biosystems, Foster City, Calif.), and the PCR reaction was analyzed using the Sequence Detection System Ver. 2.1. For expression analysis all samples were normalized to the ribosomal RNA 18S signal and the expression of EGFP in transgenic tissues was compared to the background signal in WT testis.

Figure 2:
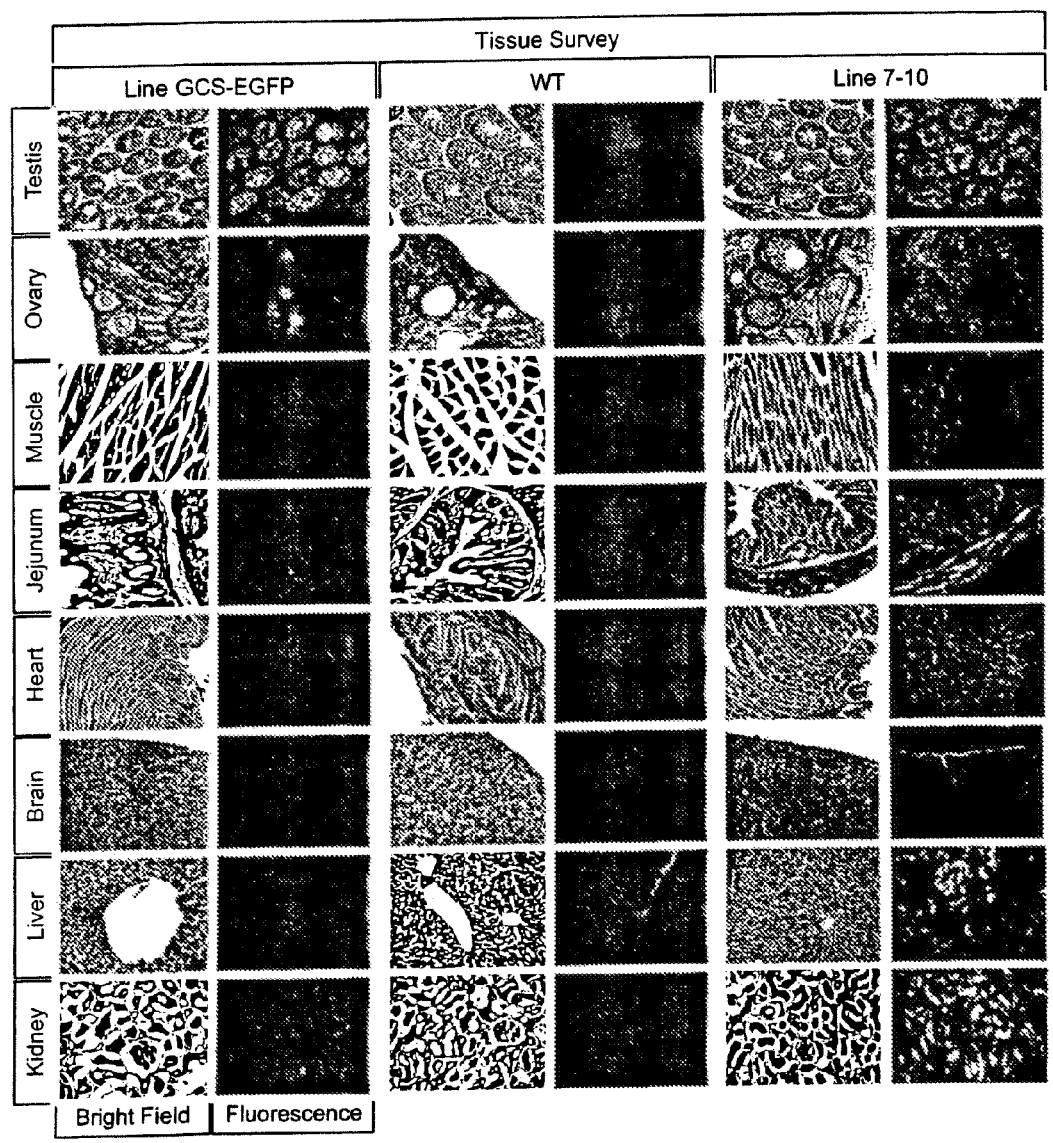
FIG. 2 shows that EGFP expression is specific to germ cells in the GCS-EGFP line. Tissues (testis, ovary, muscle, jejunum. heart, brain, liver, and kidney) from adult rats were fixed, snap frozen, sectioned, and imaged using an EGFP fluorescent filter and photographed. Adjacent sections were stained with H&E. In GCS-EGFP rats, only germ cells in the seminiferous tubules in the testis and eggs in the ovary express EGFP. There was very little auto fluorescence in the tissues from the WT Sprague Dawley rats. EGFP was expressed in a subset of cells in all of the tissues examined in the 7-10 ROSA-EGFP transgenic line.

Four lines of ROSA-EGFP transgenic rats were generated, designated as lines Hsd:SDTgN(ROSA-EGFP) 2-4, 4-2, 7-9 and 7-10 Reh; three of which contained the transgene on autosomes and one (7-9) that harbored the transgene on the Y chromosome. In two (line 4-2 and 7-9) of the four lines, one with an autosomal integration and the other Y-linked, there was no apparent EGFP expression in any of the 15 tissues examined, either macroscopically or microscopically. In the 7-10 line, EGFP was expressed in every organ examined, but the abundance of EGFP fluorescence varied between organs and often appeared cell-specific within an organ (FIG. 2). In the fourth line (line 2-4, designated GCS-EGFP), expression of EGFP appeared limited to the germ cells (FIG. 1). The two lines without obvious transgene expression were discarded and the other two were bred to transgene homozygosity. Progeny from both lines develop normally and do not display obvious abnormalities associated with transgene insertion or expression.

The EGFP expression pattern in lines 7-10 and GCS-EGFP were characterized more extensively. In the GCS-EGFP rats, EGFP fluorescence was not detectable in the brain, heart, jejunum, kidney, liver, or skeletal muscle (FIG. 2). EGFP expression was robust in ovulated unfertilized eggs (FIGS. 1G, 1H) and in adult male germ cells including mature sperm cells (FIGS. 1E, 1F). Expression of EGFP mRNA, analyzed by quantitative PCR, demonstrated that expression of EGFP was confined to the testis and ovary (not present in muscle, fat, liver, small intestine, large intestine, spleen, kidney, heart, submandibular, brain, and stomach) (Table I). In line 7-10, EGFP expression was observed in all tissues examined (FIG. 2); there was robust EGFP fluorescence in the testis, ovary, and kidney. Expression in the testis was evident in germ, Sertoli and Leydig cells. In the ovary, EGFP fluorescence was substantial in both germ and cumulus cells. Quantitative PCR of RNA isolated from this subset of organs confirmed the expression of EGFP and identified the ovary, testis, epididymis, and spleen as the sites of highest EGFP expression (Table I).

TABLE I

Relative EGFP expression in tissues of GCS-EGFP and 7-10 ROSA-EGFP rat lines.

| | Transgenic Lines | |
| Tissue | GCS-EGFP | Line 7-10 |
| --- | --- | --- |
| Skeletal muscle (soleus) | Bkg | 2.7 |
| White Fat | Bkg | 5.6 |
| Liver | Bkg | 5.8 |
| Jejunum | Bkg | 5.7 |
| Colon (proximal) | Bkg | 5.6 |
| Spleen | Bkg | 8.6 |
| Kidney | Bkg | 7.1 |
| Heart (right ventricle) | Bkg | 6.9 |
| Submandibular | Bkg | 1.5 |
| Brain (frontal lobe) | Bkg | 5.2 |
| Stomach | Bkg | 6.9 |
| Ovary | 5.1* | 8.6 |
| Testis | 11.7 | 9.6 |
| Epididymis (cauda) | 6.1 | 9.7 |

Total RNA was subjected to real time quantitative PCR as described above. Each value represents the ratio of EGFP mRNA relative to the background (Bkg) value in WT.
*6 week old GCS-EGFP females were injected intraperitoneally with 20 units of Gestyl (Organon Pharmaceuticals, West Orange, NJ) sacrificed and ovaries collected 72 hours after treatment.

EXAMPLE 2

Characterization of the Transgene Insertion and Assignment of the Transgene Chromosomal Position FISH Analysis.

Rat embryonic fibroblasts were isolated from E15.5 homozygous embryos by standard procedures (Ref. 18). Slides for cytogenetic analysis were prepared essentially as previously described (Ref. 19). Briefly, cell cultures were treated with 0.2 mg/ml of 5'-bromo-2'-deoxyuridine (BrdU) for 17 hours. Subsequently, the cells were washed three times and cultured for 6 h in medium supplemented with 0.05 µg/ml thymidine. Mitotic figures were accumulated by adding 0.05 µg/ml Colcemid (Sigma Aldrich. St. Louis, Mo.) during the final 30 min., and metaphase cells were harvested by mitotic shake-off, a procedure which selects cells which have entered mitosis and have become morphologically rounded which allows them to become easily detached from the culture plate by gentle shaking. The cells were resuspended in 0.07 M KCl at room temperature for 10 min, washed, and fixed in three dilutions of methanol:acetic acid (9:1, 5:1, and 3:1). Dual-color FISH analysis was performed using a biotinylated (Nick Translation Systems, GibcoBRL, Carlsbad, Calif.) BAC DNA probe for the Grik/Ncam/Kcjnb/Mx1 genes and a digoxigenin-11-dUTP labeled (DIG-NICK Translation Mix, Roche Diagnostics GmbH, Mannheim, Germany) DNA probe for EGFP (Ref. 20). Approximately 500 ng of the co-precipitated probes along with about 15-fold excess of sonicated total rat genomic DNA were co-hybridized to each slide. Detection of the dual-color labeling was performed using a mixture of Rhodamine-conjugated antidigoxigenin and FITC-conjugated avidin (Invitrogen/GibcoBRL Carlsbad, Calif.). The chromosome preparations were washed, counter-stained, and the fluorescence signals were visualized as described previously (Ref. 21).

Two PCR based methods were used as a first approach to identify the DNA regulatory regions that target the germ cell lineage, and to identify the structural gene that marks this lineage, the Universal Genome Walker Kit (BD Biosciences, San Jose, Calif.) and inverse PCR on the 3'transgene sequence. At most, 50 bp of flanking sequence was obtained by both methods, which was insufficient to identify a unique sequence in the rat genomic database. Most transgenes generated by microinjection are present in multiple copies and may contain small stretches of endogenous DNA between copies of the transgene (Ref. 22). A genomic dot blot analysis of the transgene insertion using an EGFP probe indicated 5 copies of the transgene were incorporated in the genome. Southern analysis using probes to the EGFP and SV40 regions of the transgene indicated there where two copies oriented in a tail-tail pattern. With multiple copies of the transgene present, PCR based methods to identify flanking DNA are often less effective due to multiple priming sites.

Figure 3:
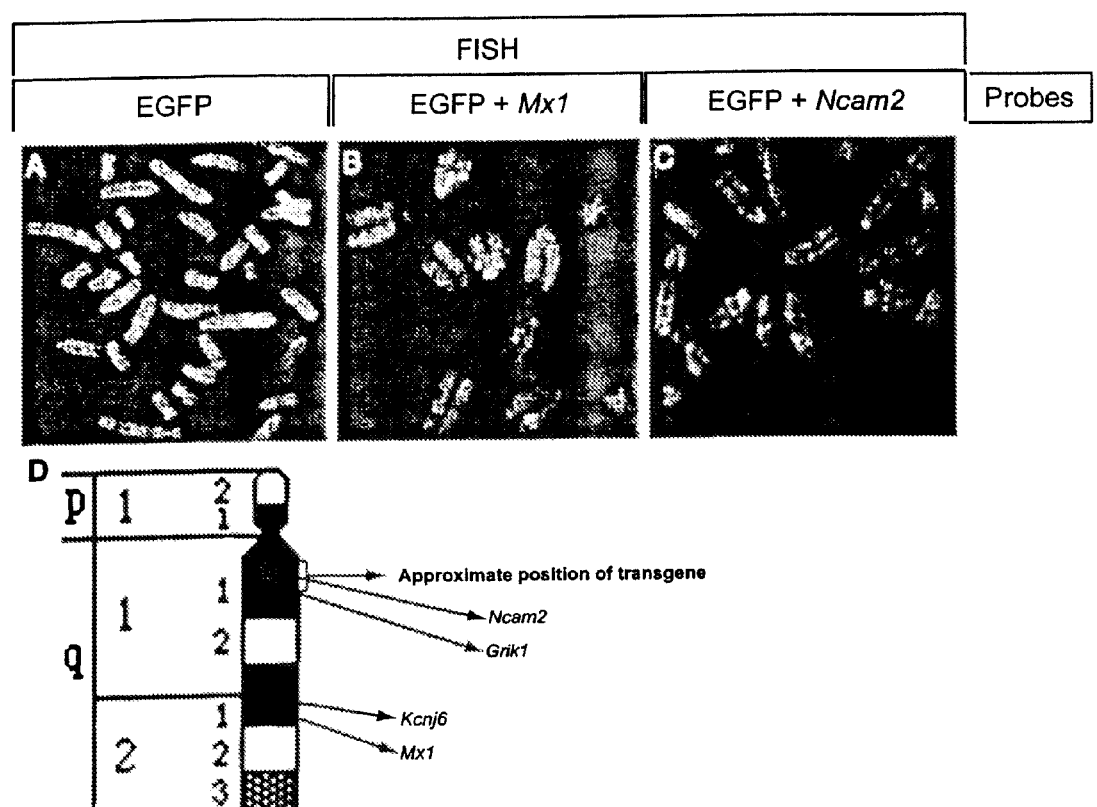
FIG. 3 shows that FISH analysis of the GCS-EGFP line places the transgene on rat chromosome 11. (A) Single labeling of EGFP (red signal) places the transgene on chromosome 11; (B) Dual labeling with an EGFP probe (red) and Mx1 probe (green) places the transgene proximal to Mx1. (C) Dual labeling with an EGFP probe (red) and Ncam2 probe (green) places the transgene very close to Ncam2. (D) Diagram of the relative position of the transgene based on FISH analysis.

To determine the chromosomal location of the transgene, fluorescence in situ hybridization (FISH) analysis was performed on GCS-EGFP homozygous colcemid-treated embryonic fibroblasts. The chromosome preparation was spread onto slides and an EGFP probe was used for hybridization (FIG. 3A). The transgene was assigned to chromosome 11 in the q11-q12 region. To narrow the region, dual hybridization was performed using an EGFP probe and a BAC clone probe that contained a known gene on chromosome 11; (Mx1) (FIG. 3B). The EGFP signal was proximal to Mx1. Another BAC clone containing Kcnj6, a known gene on rat chromosome 11 was also used as a probe and the EGFP was proximal to Kcnj6. Two other genes that were proximal to Mx1 and Kcnj6, namely Ncam2 (FIG. 3C) and Grik1 were chosen. The EGFP insertion site was proximal to Grik1 and in very close proximity to Ncam2 (FIG. 3D).

EXAMPLE 3

Figure 4:
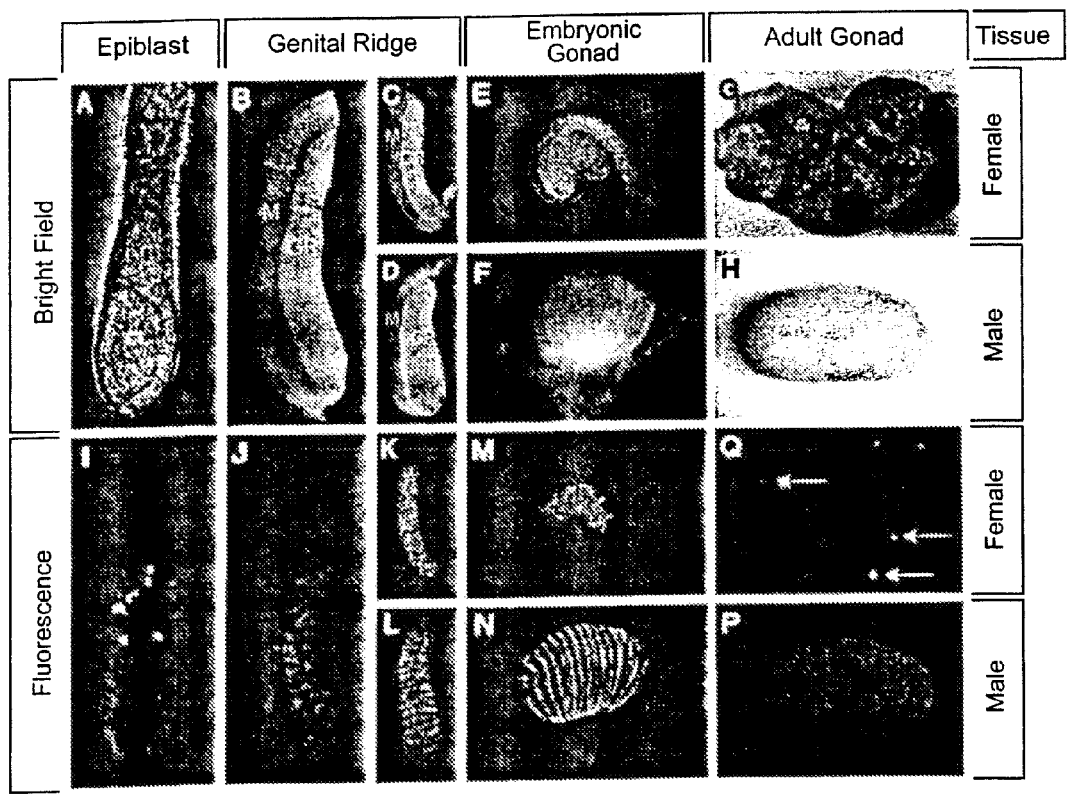
FIG. 4 shows that the EGFP expression during development is limited to germ cells. (A-F) GCS-EGFP homozygous embryos at the following developmental stages—(A) epiblast E8.5, (B) early genital ridge E12.5, (C) female genital ridge E15.5, (D) male genital ridge E15.5, (E) female embryonic gonads E19.5 and (F) male embryonic gonads E19.5, GCS-EGFP homozygous adult (G) ovary and (H) testis. (I-P) Images of same specimens in (A-H) photographed using an EGFP fluorescent filter. Arrows in O indicate the location of fluorescent eggs in the cumulus masses.

Transgene is Expressed in the Epiblast, Genital Ridge, Embryonic Gonads, and Adult Germ Cells The EGFP expression pattern in post-implantation embryos (E8.5-E19.5) were examined by fluorescence microscopy. EGFP fluorescence was first observed in the proximal epiblast with a small population of cells displaying strong fluorescence on E8.5 (FIGS. 4A, 4I); these are conceivably primordial germ cells (PGC). In E13.5 embryos, the genital ridge (FIGS. 4B, 4J) showed strong fluorescence while the adjacent mesonephros was devoid of an EGFP signal. In E15.5 embryos, the male and female genital ridges can be distinguished from each other in that the male genital ridge (FIGS. 4D, 4L) exhibits a distinct cording pattern while the female ridge is mottled (FIGS. 4C, 4K). The genital ridges from both sexes of the GCS-EGFP rats were strongly fluorescent. The male and female embryonic gonads (FIGS. 4M, 4N) also showed strong EGFP fluorescence while the surrounding somatic support tissues were negative. EGFP fluorescence in the adult ovary of GCS-EGFP rats was confined to eggs in all stages of maturation (FIGS. 4G, 4O) while in the adult testis EGFP fluorescence was robust only within the seminiferous tubules (FIGS. 4H, 4P).

Figure 5:
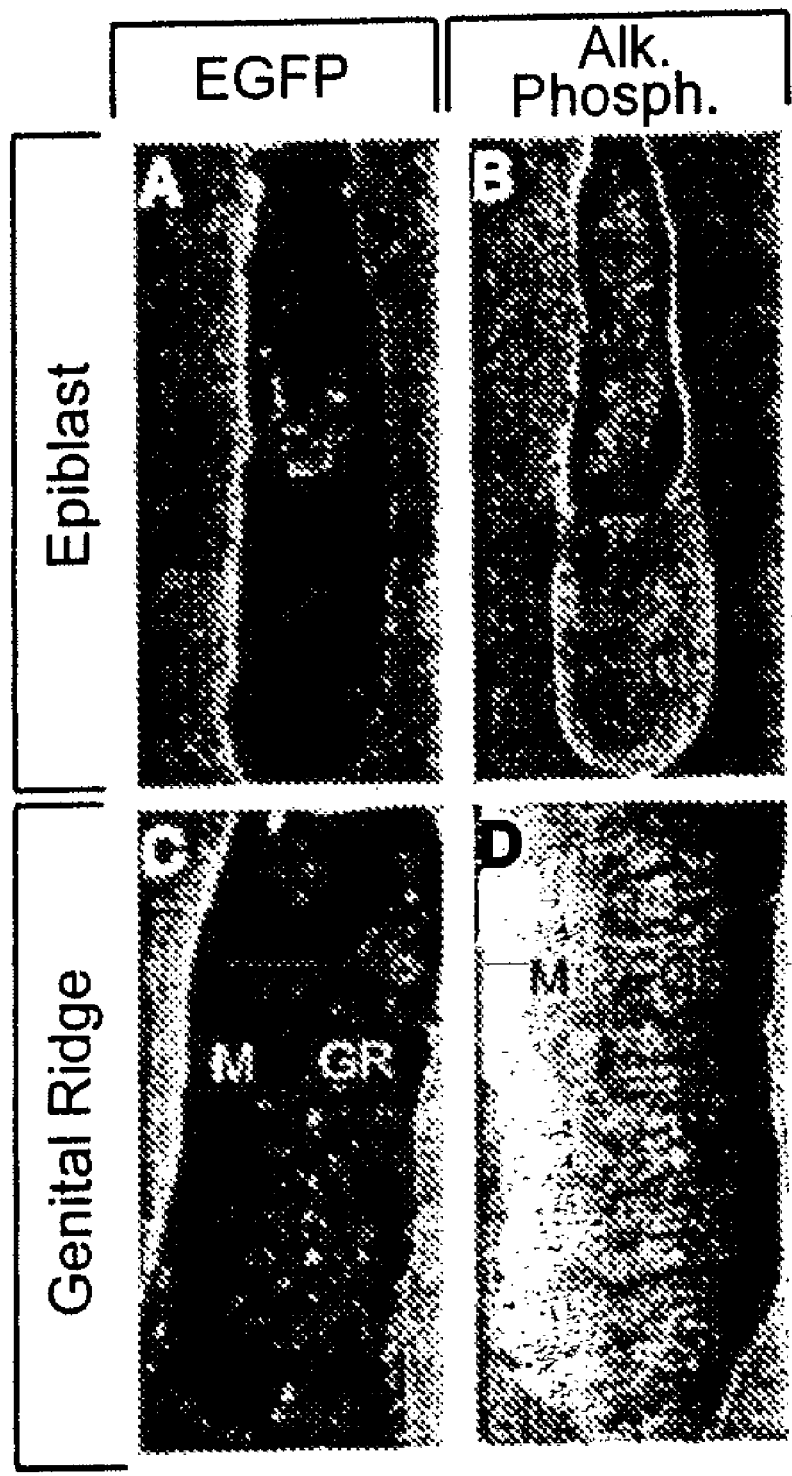
FIG. 5 shows that the EGFP expression colocalizes with the expression of alkaline phosphatase, a marker for germ cells. (A, B) GCS-EGFP homozygous embryos at E8.5; (A) Phase-contrast and fluorescent overlay reveals EGFP expression is localized to the extra-embryonic portion of the epiblast with a population of the EGFP cells located in the proximal region. (B) Alkaline phosphatase activity is high in the same subpopulation of cells. (C, D) Genital ridges from E13.5 GCS-EGFP embryos, (C) Phase-contrast and fluorescent overlay reveals EGFP expression is localized to the genital ridge (GR) and not the adjacent mesonephros (M) tissue. (D) Alkaline phosphatase activity (red orange) is highest in the genital ridge.

As PGCs are identified principally by location, morphology and high alkaline phosphatase activity, experiments were carried out to determine if there was concordance between cells showing GFP expression and cells expressing high alkaline phosphatase activity. Cells in the proximal region of the epiblast and cells in the genital ridge had very high alkaline phosphatase activity (FIGS. 5B, 5D), and this same region also displayed abundant number of cells with robust expression of EGFP (FIGS. 5A, 5C). Thus, early and late primordial germ cells in the GCS-EGFP rat appear to express EGFP.

EXAMPLE 4

Transgene Expression in Pre-Implantation Embryos

Figure 6:
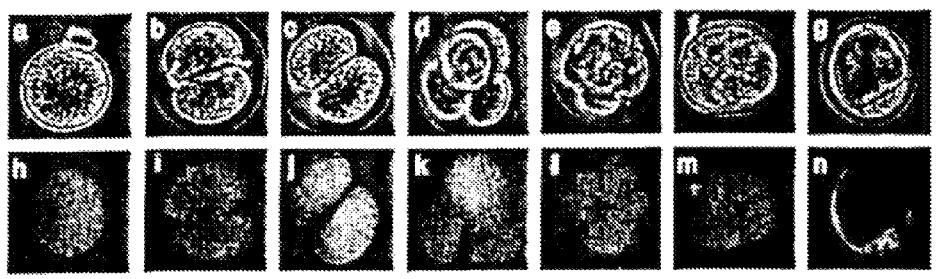
FIG. 6 illustrates the EGFP expression in pre-implantation embryos. (A) EGFP expression in embryos from a GCS-EGFP homozygous female mated to a WT SD male. EGFP is expressed in the one-cell egg, increases in the late 2-cell embryo and is expressed in the blastocyst in the inner cell mass and trophoblast cells. (B) EGFP expression in embryos isolated from a WT SD female mated to a GCS-EGFP homozygous male. EGFP expression is first detectable in the late 2-cell when the zygotic genome is activated, it is expressed throughout preimplantation development and then becomes limited primarily to the inner cell mass of the blastocyst. (a-g) Phase-contrast photomicrographs of embryos at: (a) one-cell, (b) early two-cell, (c) late two-cell, (d) four-cell, (e) 8 or 16-cell, (f) morula, and (g) early blastocyst, (h-n) fluorescent photomicrograph of the same eggs in (a-g). (C) No auto fluorescence is detected in WT embryos. (D) EGFP expression in delayed blastocysts isolated on E8.5 from a WT SD female mated to a GCS-EGFP homozygous male. Expression of EGFP is limited to the ICM; (a) Phase-contrast, (b) Fluorescent image of (a), and (c) overlay.
Figure 6:
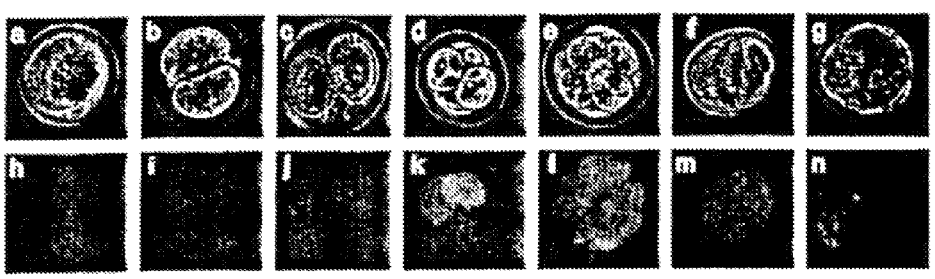
Figure 6:
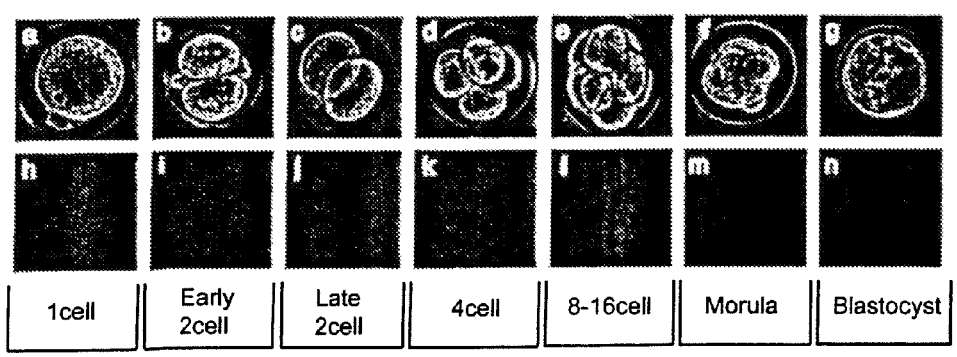
Figure 6:
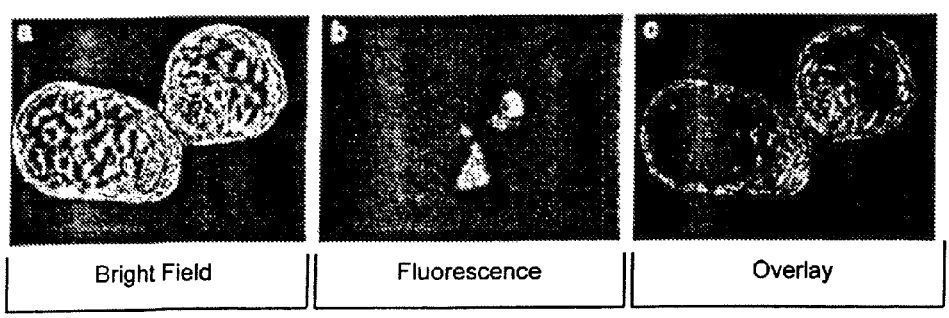

EGFP expression in pre-implantation embryos were characterized to determine the temporal and spatial patterns of expression during early germline delineation. To accomplish this, homozygous females and males were mated to WT rats and embryos were collected at one-cell, two-cell, four-cell, morula, and blastocyst stages of development and examined for EGFP fluorescence. In fertilized eggs collected from transgenic females there was uniform robust EGFP expression from the one cell to the morula stages of development (FIGS. 6A, a-f and h-m). There was a significant, reproducible increase in the expression of EGFP at the late two-cell stage onward, the known time of transition from maternal to zygotic based transcription (Ref. 23). The initiation of EGFP expression at the late two-cell stage was confirmed in embryos collected from WT females mated with transgenic males. In eggs from this cross, there is no maternal EGFP message or protein and thus he onset of transgene expression was established. There was no EGFP fluorescence in either the one or early two-cell eggs (FIGS. 6B, a-b and h-i). In contrast, there was weak but discernable expression in both blastomeres of the late two-cell stage eggs (FIGS. 6B, c and j) indicating that transgene expression is initiated during the earliest period of zygotic transcriptional activation.

Expression in the early to mid blastocyst stage of development was localized to both the inner cell mass and trophoblast (FIGS. 6A and 6B, g and n). This non-ICM restricted pattern of expression may be due to active transcription of the transgene in these two compartments or more likely, may be a reflection of the extended half-life of EGFP (~20 hours). To discriminate between these two possibilities, delayed implantation was induced in WT females mated with transgenic males, collected blastocysts at E8.5 and examined them for the localization of EGFP expression. In all of the blastocysts examined (n=50), EGFP fluorescence was localized exclusively to the ICM with no discernable expression in trophoectoderm (FIGS. 6D, a-c). This result suggests that EGFP expression is limited to the ICM, the sole derivative of the germ cell lineage.

EXAMPLE 5

Transfer of GCS-EGFP Seminiferous Tubule Cells to Recipient Testes

A. Seminiferous Tubule Cell Isolation from Testis.

Seminiferous tubules were isolated from the testes of 23 day old homozygous GCS-EGFP rats. The tubules were mechanically disaggregated and enzymatically digested with dispase (Invitrogen/GibcoBRL Carlsbad, Calif.), dissociated into a cellular suspension, and filtered through a 20 μm nylon mesh. Cells were then counted and resuspended at a concentration of $1 \times 10^7$ cells/ml (Ref. 24).

B. Germ Cell Transplantation.

Twelve day-old WT Sprague Dawley male rats were injected intraperitoneally with 12.5 mg/kg of busulfan (4 mg/ml in 50% DMSO) and used as recipient males at 24 days of age. Donor cells were loaded into an injection needle fashioned from a 100 μl glass capillary microcaps (Cole-Parmer Instruments Co., Vernon Hills, Ill.) and cells were transplanted into the seminiferous tubules of an anesthetized recipient rat by retrograde injection through the rete testis (Ref. 25-26). Trypan blue was added to the cell suspension to visualize transfer into the tubules. Recipient rats were analyzed for donor cell colonization on day 30 or 60 after transfer by direct visualization of EGFP expression using a fluorescent Nikon SMZ1500 stereomicroscope. The seminiferous tubules were dissected from the testis and processed for the quantitation of soluble GFP as described (Ref. 24). The testis lysates were assayed for fluorescent intensity using recombinant EGFP with a carboxyl-terminal histidine tag as a standard.

Figure 7:
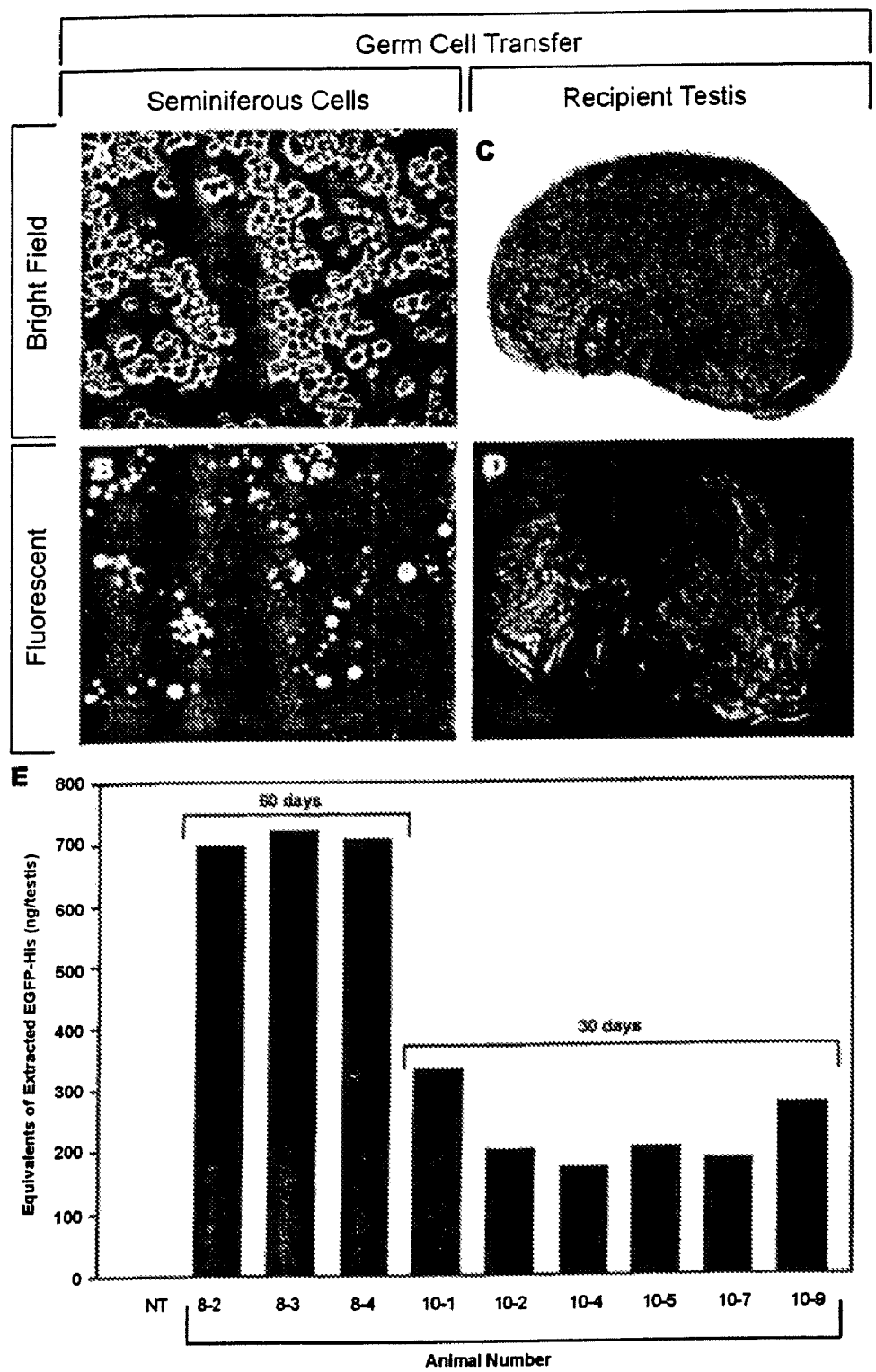
FIG. 7 shows that disaggregated seminiferous tubule cell preparations from GCS-EGFP rats colonize the seminiferous tubules of wild-type rats depleted of endogenous germ cells. (A) Unsorted seminiferous tubule preparation from a GCS-EGFP homozygous male. (B) Only a subset of unsorted seminiferous tubule cells shown in (A) express EGFP and are germ cells. (C) Recipient testis 60 days post-transfer. (D) Fluorescent photomicrograph of specimen shown in (C) showing extensive colonization by GCS-EGFP germ cells. (E) Quantitation of the abundance of GFP in recipient testis 30 days (10-1, 10-2, 10-4, 10-5, 10-7, 10-9) and 60 days (8-2, 8-3, 8-4) following transfer. Values represent the quantity of extracted GFP/testis. NT (uninjected testis).

Unsorted seminiferous tubule cells from GCS-EGFP rats (FIGS. 7A, 7B) were transferred to the testis of recipient males to establish the efficiency of this heterogenous population of cells to take residence in a recipient testis. Colonization efficiency is the measure of the inherent stem cell activity of a given population of cells and presumably the germline stem cells constitute a very small proportion of the total seminiferous tubule cell preparation of an adult testis (Ref. 25, 27-29). Recipient males were sacrificed at either 30 or 60 days following cell transfer, the testis examined by fluorescent microscopy and the entire tubular mass processed for quantification of the abundance of GFP. The testis from all recipient males that were sacrificed 30 days after receiving seminferous tubule cells from GCS-EGFP rats had abundant GFP expressing cells distributed throughout the tubules (FIGS. 7C and 7D), and had quantities of GFP/testis that ranged between 200-300 ng. Extending the time of colonization from 30 to 60 days approximately doubled the abundance of GFP per testis (FIG. 7E).

EXAMPLE 6

Purification and Transplantation of Germ Cells

A. Materials and Chemicals.

Dispase and rat-tail collagen I-coated culture dishes were from Fisher, Inc. Cell culture media, phosphate-buffered saline (PBS), non-essential amino acids, MEM vitamin solution, L-glutamine solution and trypsin-EDTA solutions (0.05% w/v trypsin with 0.2 g/L EDTA.4Na; or 0.25% w/v trypsin with 0.38 g/L EDTA.4Na), B27 supplement, B27 minus vitamin A supplement, and antibiotic (cat. 15070-063) and antibiotic-antimycotic (cat. 15240-062) solutions were from Invitrogen, Inc. Bovine serum albumin (BSA) was from Calbiochem, Inc. Fetal bovine serum (FBS) was from Atlanta Biologicals, Inc. Blocking reagent was from Roche Applied Sciences, Inc. Mitomycin-C, Cy3-conjugated anti-vimentin IgG (clone V9), mouse laminin, mouse epidermal growth factor (EGF), rat glial cell line-derived neurotrophic factor (GDNF), bovine apo-transferrin, human basic fibroblast growth factor (bFGF), d-(+)-glucose, d-biotin, ascorbic acid, sodium pyruvate, putrescine, progesterone, beta-estradiol 17-cypionate, insulin, sodium selenite, 2-mercaptoethanol (ME), dl-lactic acid and all fatty acids were from Sigma, Inc. AlexaFlour-594-conjugated, goat-anti-rabbit IgG and Hoechst 33342 were Invitrogen, Inc. Mouse leukemia inhibitory factor/ESGRO (LIF) was from Chemicon, Inc. Rat GFRα1-Fc Chimera (GFRα1) was from R&D systems, Inc. Feeder cell lines, M2-10B4 mouse stromal, AFT024 embryonic liver, C166 mouse yolk sac endothelial, Rat-1 fibroblasts and primary MEFs, were from ATCC, Inc., unless otherwise acknowledged. Primary Rat embryonic fibroblasts (Day 14.5) were a gift from Lynda DooLittle.

B. Spermatogonial Stem Cell Index (SSCI).

To determine SSCI values, the relative abundance of 10 rat SSCI transcripts (Ref. 24) in GCS-EGFP$^+$ germ cell samples were determined by real-time PCR. Real-time PCR analysis was performed using the ABI Prism 7900HT Sequence Detection System (Applied Biosystems) (Ref. 30). Germ cell (GCS-EGFP$^+$) samples were purified from different experimental cultures by fluorescence-activated cell sorting (FACS) and then total RNA was isolated from each sample using the RNAqueous Micro kit (Ambion, Inc.). Purified RNA samples were quantified using the RiboGreen RNA quantitation method (Invitrogen, Inc.) and then 5-35 ng of each sample was reverse transcribed to cDNA in a 20-μl reaction using the SuperScript III First Strand Kit (Invitrogen, Inc.). The cDNA samples were diluted 1:10 or 1:100, and then 5 μl was used for PCR reactions using the rat SSCI and 18S ribosomal RNA subunit primer sets (Table II). PCR was performed using the SYBR Green PCR Master Mix (BIO RAD, Inc). The threshold cycle ($C_T$) generated by each primer-set for SSCI marker transcripts was normalized to the $C_T$ generated by the primer-set specific for the 18S ribosomal RNA subunit by the following formula: Relative transcript abundance= $\frac{1}{2}(C_T \text{ of marker transcript} - C_T \text{ of 18S RNA subunit})$ (Ref. 31-32). Relative abundance values were normalized to 0.02 as a maximal value from each primer pair within a set of germ cell samples. Each set of germ cell samples analyzed included standard cDNA prepared from Lam$_B$ (D0) and Lam$_{NB}$ (D0) germ cells. SSCI values are equal to the mean of the relative abundance values determined for all 10 of the SSCI marker transcripts in a given germ cell sample.

TABLE II

Real Time PCR Primer Sets For Determining Spermatogonial Stem Cell Index Values
(SEQ ID NOS 5-26, respectively, in order of appearance).

| Gene | Accession Number | Primer sequence | | Common Name |
|---|---|---|---|---|
| 18S | V01270 | F aagtccctgccctttgtacaca<br>R gcctcactaaaccatccaatcg | (1683-1704)<br>(1743-1722) | 18S ribosomal RNA |
| Snap91 | NM_031728 | F tttgatccaggctaccaacga<br>R gcccgctcaaagagggtatc | (188-208)<br>(256-237) | Synaptosomal-associated protein 91 kDa homolog; Ap180 |
| Fgfr3 | NM_053429 | F ctgaccgcggcaattacac<br>R tgtacgtctgccggatgct | (644-662)<br>(706-688) | Fibroblast growth factor receptor 3 |
| GFRa1 | NM_012959 | F tcgggtagcacacacctctgt<br>R gaggcaccagcgagaccat | (1478-1498)<br>(1542-1524) | GDNF family receptor alpha 1 |
| Ret | NM_012643 | F tggcacacctctgctctatg<br>R tagacgccatagagatactg | (151-170)<br>(240-221) | Ret proto-oncogene |
| IMP2 | XM_221343 | F tagagaacgtggagcaagtc<br>R tcgaactgatgcccacttaac | (827-846)<br>(1088-1068) | IGF-II mRNA-binding protein |
| F2r | NM_012950 | F agttcgggtccggaatgtg<br>R accggtcaatgcttatgac | (600-618)<br>(695-677) | Coagulation factor II receptor; PAR1; Thrombin receptor |
| Aebp1 | XM_223583 | F accaactgcctggagctctct<br>R acctgctccatgaaggttagc | (2965-2985)<br>(3080-3060) | Adipocyte enhancer binding protein 1 |
| Midn | XM_234902 | F acccggtgcagtcattgag<br>R gcagaatggtgccgatgtc | (699-717)<br>(829-811) | Midnolin |
| Sdc4 | NM_012649 | F agggcagcaacattttgaaa<br>R gcgaagaggatgcccactac | (434-454)<br>(509-490) | Syndecan 4 |
| Hey1 | XM_342216 | F tgcagatgactgtggatcacc<br>R tcagataacgggcaacttcag | (1919-1939)<br>(2053-2033) | Hairylenhancer-of-split related with YRPW motif 1; Herp2 |

F Forward Primer, R Reverse Primer

Figure 8:
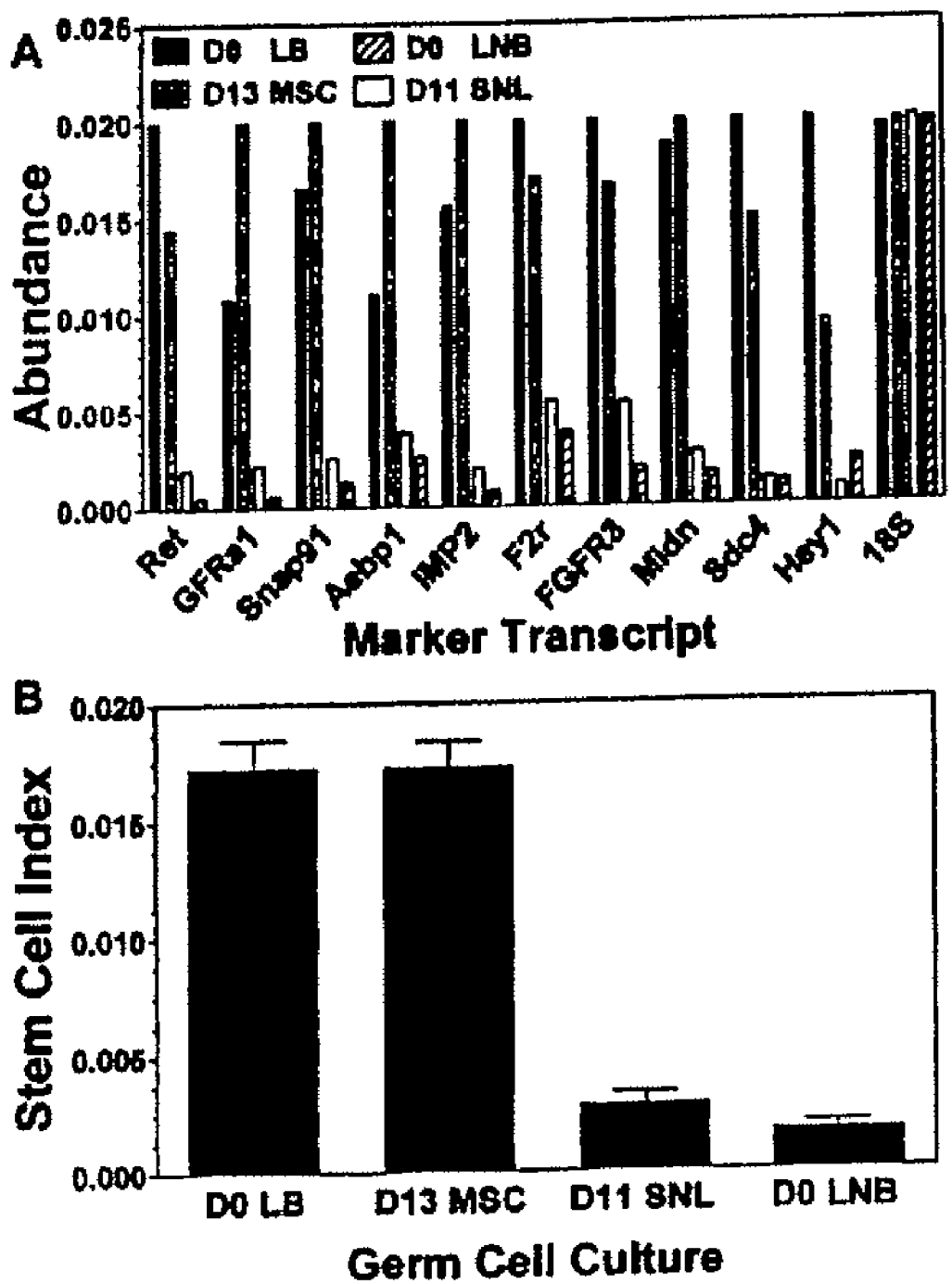
FIG. 8 illustrates the spermatogonial stem cell index (SSCI) for rat germ cell cultures. (A) Relative abundance of 10 transcripts associated with spermatogonial stem cell activity was measured in cultures of GCS-EGFP$^+$ Lam$_B$ germ cells by real-time PCR. D0 Lam$_B$ germ cells (D0 LB) were isolated fresh or purified from somatic feeder cells by FACS after 13 days on MSC1 cells (D13 MSC) or 11 days on SNL cells (D11 SNL). D0 Lam$_{NB}$ germ cells (D0 LNB) were also analyzed. Rat gene symbols are listed for each transcript on the X-axis. (B) Rat SSCI values for germ cell cultures analyzed in panel A. The SSCI values are equal to the mean of the relative abundance of the transcripts in panel A (±SEM of relative abundance values, n=10 marker transcripts).

The 18S ribosomal transcript is expressed at essentially the same relative abundance/ng total RNA in either pre-meiotic ($Lam_B$) or meiotic ($Lam_{NB}$) rat germ cell populations (Ct=24.1±0.46, ±SD, n=13 different primary cultures). FIG. 8 represents the relative abundance of ten transcripts that mark spermatogonial stem cell activity in $Lam_B$ germ cells after culture on SNL or MSC-1 cells. Consistent with microarray results (Ref. 24), real-time PCR analysis established that these ten transcripts are relatively abundant in D0 $Lam_B$ germ cells and do not decline in abundance after maintenance for 13 days on MSC-1 feeders (FIG. 8A). In contrast, the abundance of these same transcripts decreased markedly in $Lam_B$ germ cells by 11 days after culture on SNL cells, acquiring a profile more comparable to $Lam_{NB}$ germ cells (FIG. 8A). The mean of the relative abundance values determined for these 10 marker transcripts yielded the stem cell index (SSCI) (FIG. 8B).

C. Testicular Cell Cultures.

Seminiferous tubules were isolated from testes of 22-23 day old homozygous GCS-EGFP or wild type (WT) Sprague Dawley rats. The tubules were enzymatically and mechanically dissociated into a cellular suspension to generate cultures of testis cells (Ref. 25). The testis cell cultures were then used to isolate enriched populations of laminin-binding ($lam_B$) or laminin-non-binding ($lam_{NB}$) germ cells and tubular somatic cells (Ref. 24-25). Cultures of interstitial cells were prepared from 23 day old rats (Ref. 33). These freshly isolated testis cell populations are referred to as day 0 (D0) cultures. Day 0 GCS-EGFP $Lam_B$ germ cells contain >90% type A spermatogonia and ~5% somatic testis cells at this stage (Ref. 24-25). In contrast, D0 $Lam_{NB}$ germ cells are depleted of stem cell activity and consist of ~96% differentiated spermatogonia plus spermatocytes, and only ~4% type A spermatogonia (Ref. 24-25).

Figure 9:
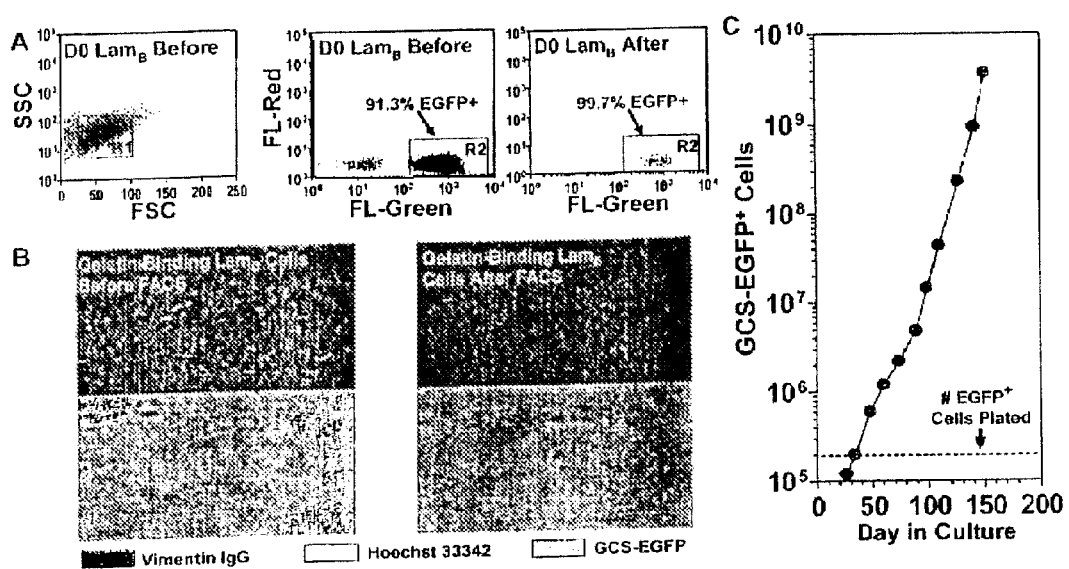
FIG. 9 illustrates the purification and proliferation of EGFP$^+$ spermatogonia in vitro. (A) Flow cytometric properties of D0 GCS-EGFP$^+$ Lam$_B$ germ cells before and after purification by FACS. (Left) Side (SSC) versus forward (FSC) scatter plot. Region 1 (R1) contained ~92% of the total population. (Center) ~91% of Lam$_B$ cells from R1 were EGFP$^+$ germ cells (R2). (Right) Lam$_B$ cells collected from R1 and R2 were >99% EGFP$^+$ germ cells. (B) Selection of vimentin$^+$ (red), gelatin-binding somatic cells from the D0 GCS-EGFP$^+$ Lam$_B$ germ cell (green) population before (left) and after (right) collection of the EGFP$^+$ population by FACS. Cells were selected for 3 days on gelatin-coated plates in S-medium prior to harvesting un-bound germ cells, and labeling bound cells with anit-vimentin IgG and Hoechst 33342 (blue). (C) Expansion of FACS purified EGFP$^+$ spermatogonia in culture on MEFs. Cultures were initiated with 2×10$^5$ FACS-purified EGFP$^+$ cells (dashed line).

To propagate rat spermatogonial stem cells from primary culture, EGFP+ spermatogonia were isolated from GCS-EGFP $Lam_B$ germ cells (D0) by fluorescence-activated cell sorting (FACS), as shown in FIG. 9A. A population of >99.7% pure EGFP+ cells was obtained, and then cultured for two days on gelatin in the serum-containing S-medium (Ref. 34) to further remove contaminating somatic cells (FIG. 9B). EGFP+ spermatogonia remained loosely bound to the culture plate or in suspension following selection on gelatin-coated plates and were then passaged after 2 or 3 days into 3.5 cm or 10 cm culture dishes containing $5.2 \times 10^4$ mitomycin-C treated primary mouse embryonic fibroblasts (MEFs)/$cm^2$. in the serum-free SA-medium. Cultures of EGFP+ spermatogonia were passaged between 1:2 to 1:8 dilutions onto fresh MEFs every 8-14 days at 2 and $4 \times 10^4$ EGFP+ cells/$cm^2$. A 0.05% trypsin-EDTA solution was used to dissociate cultures prior to each passage, or before purifying EGFP+ spermatogonia by FACS for determination of stem cell marker transcript concentrations. The number of EGFP+ cells recovered during each passage was determined by counting them on a hemocytometer under an inverted fluorescent microscope.

D. Germ Cell Transplantation and Colonization.

WT Sprague Dawley rats at 12 days of age were injected (i.p.) with 12.5 mg/kg busulfan (4 mg/ml in 50% DMSO) and then used as recipient males at 24 days of age. Donor tgGCS-EGFP rat cells isolated from culture were loaded into injection needles fashioned from 100 μl glass capillary tubes at concentrations ranging from $10^3$ to $10^5$ EGFP+ cells/65 μl culture media containing 0.04% trypan blue. The entire 65 μl volume was then transferred into the seminiferous tubules of anesthetized rats by retrograde injection through the rete of their right testes (Ref. 35). The number of EGFP+ colonies formed/testis were scored by using an Olympus IX70 fluorescence microscope (Olympus, Inc) to visualize donor cell transgene expression in the seminiferous tubules at 32 days following transplantation. Images of whole recipient testis were taken with a Nikon SMZ1500 fluorescence stereomicroscope. Frozen cross-sections were prepared from the right (transplanted) and left (non-transplanted) testis of some recipients at 62 days following transplantation, as described (Ref. 15), except the testes were fixed in 4% paraformaldehyde at 4° C. overnight (12 hr) and then sequentially equilibrated overnight in 10%, 20% and 30% sucrose solutions prior to sectioning. Sections were counter-stained for 25 min at 22-24° C. in PBS containing 5 μg/ml Hoechst 33342 dye and/or 5 μg/ml Cy3-anti-vimentin IgG. Some sections were also treated for 4 hr at 22-24° C. with anti-Crem tau IgG (sc-440, Santa Cruz, Inc) diluted 1:1000 in Roche blocking (1% w/v) reagent and then indirectly labeled with a secondary AlexaFuor594 anti-rabbit IgG.

E. Immunocytochemistry.

Cultures of germ cells (2 $cm^2$) were washed twice with serum-free DHF12 medium (0.8 ml/well) and then fixed for 7.5 min with 4% paraformaldehyde, 0.1M sodium phosphate, pH 7.2 (0.4 ml/well). After fixation the cells were washed 3 times with PBS (0.8 ml/well) and then incubated for 15 min in PBS containing 0.1% (v/v) Triton-X 100 (0.4 ml/well). The cells were then washed 3 times in PBS (0.8 ml/well) and non-specific, protein-binding sites were blocked by incubating the cells in 1% w/v blocking reagent (0.4 ml/well, Roche, Inc.) for 1.5 hr at 22-24° C. The blocking reagent was removed and the cells were incubated for 16 hr at 22-24° C. in primary antibodies (0.4 ml/well). The anti-Dazl-3 IgG and the preimmune-3 IgG fractions (Ref. 25) were diluted to 250 ng/ml in blocking reagent. Following incubation in primary antibodies, the cells were washed 3 times for 5 min with TBST (0.8 ml/well) to remove unbound IgG. The cells were then incubated for 40 min at 22-24° C. in conjugated, secondary antibody (0.4 ml/well) diluted to 1 μg/ml in PBS containing Hoechst 33342. Following incubation in secondary antibodies, the cells were washed 3 times for 5 min with TBST (0.8 ml/well) to remove unbound IgG and dye prior to viewing in fresh PBS (0.8 ml/well) using an inverted Olympus IX70 microscope (Olympus, Inc.).

F. Electron Microscopy.

Testis cells were fixed with 3% glutaraldehyde in 0.1M sodium cacodylate buffer, pH 7.4 followed by post fixation with in 0.1M sodium cacodylate buffer, pH 7.4 containing 1% osmium tetroxide, dehydrated with ethanol, embedded in Spurr resin in Beem capsules and polymerized overnight at 60° C. Semi-thin sections for light microscopy were cut at 1 micron, placed on glass slides and stained with filtered 1% Toluidine Blue in 1% Sodium Borate. Ultra-thin sections are cut at 80 nanometers, picked up on 200 mesh copper grids, stained with Uranyl Acetate and Lead Citrate, and documented with a JEOL 1200EXII Transmission Electron Microscope. A blind operator, with respect to the cell types being studied, gathered images randomly from cultures of each testis cell population. Thirty to forty cells/culture were scored at a magnification of 4000×.

G. Maintenance of Feeder Cell Lines

The STO (SIM mouse embryo-derived thioguanine and ouabain resistant)-neomycin-LIF 76/7 fibroblasts (SNL cells) were a gift from Allan Bradley (Ref. 36) and were maintained in Dulbbeco's Modified Eagle's Medium supplemented with 10% FBS and 1× antibiotic solution (DMEM) at 37° C./5% $CO_2$. MSC-1 Sertoli cells were a gift from Michael D. Griswold (Ref. 37) and were maintained in Dulbbeco's modified Eagle's medium:Ham's F12 medium 1:1 supplemented with 8.5% FBS and 1× antibiotic-antimycotic solution at 32.5° C./5.5% $CO_2$. Prior to culture with testis cells, feeder cell lines were prepared as previously established following treatment with 10 µg/ml mitomycin-C (Ref. 24), except for C166 yolk sac endothelial cells, which were irradiated at 10,000 rads. By similar methods, primary rat somatic testis cells were pre-treated with mitomycin-C for 2.5 hr at 32.5° C./5.5% $CO_2$, and primary mouse and rat MEFs were pre-treated with mitomycin-C for 2.5 hr at 37° C./5% $CO_2$. Day 0 $Lam_B$ spermatogonia were then plated at 4×10$^4$ cells/cm$^2$ onto feeder cells in 0.26 ml/cm$^2$ DHF12 medium containing 10% FBS and 10 µM 2ME and then were maintained at 32.5° C./5.5% $CO_2$ for 7 to 14 days prior being passed, using a 0.25% trypsin-EDTA solution, onto fresh feeder layers, or harvested to isolate tgGCS-EGFP$^+$ germ cells by FACS for SSCI measurements.

H. Flow Cytometry.

GCS-EGFP$^+$ germ cells from culture were sorted on a Becton Dickinson (San Jose, Calif.) FACStar Plus cell sorting system. CellQuest software version 3.3 was used to set the parameters and monitor the conditions during the sort. The germ cells were sorted on a forward scatter (FSC) versus side scatter (SSC) dot plot, a pulse width (FSC-width vs. FSC-height) dot plot, and an FL1 (530 nm) versus FL2 (585 nm) dot plot. The DNA content of EGFP$^+$ spermatogonia and freshly isolated rat testis cells was determined by the propidium iodide method (Ref. 38).

Figure 10:
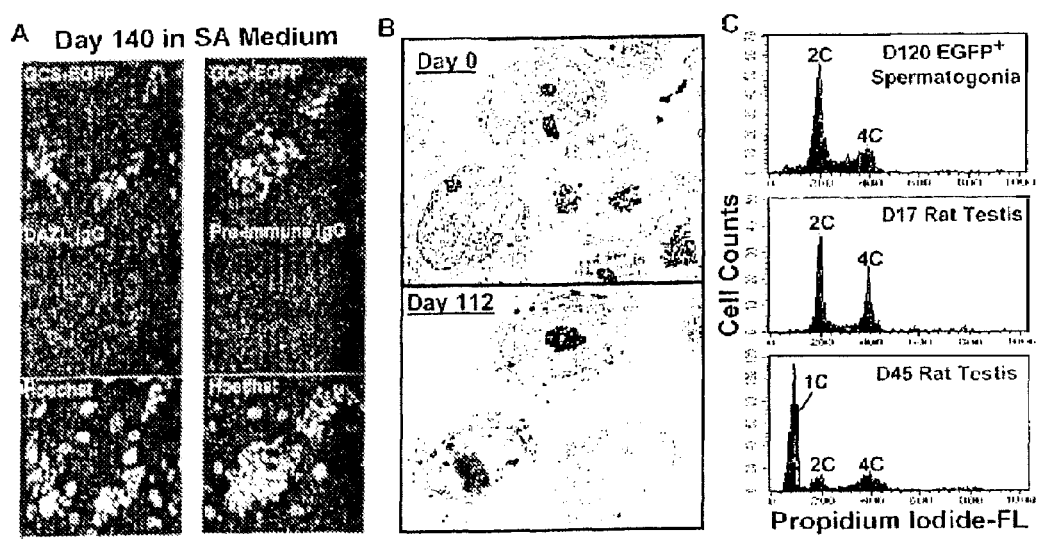
FIG. 10 illustrates the properties of EGFP$^+$ spermatogonia. (A) (Left) Colonies of EGFP$^+$ spermatogonia (GCS-EGFP) expressing DAZL (DAZL IgG) after 11 passages and 140 days in culture. Nuclei of MEF feeder cells (EGFP$^-$, DAZL$^-$) and germ cells are labeled blue with Hoechst 33342. (Right) Pre-immune IgG negative control anti-serum. (B) Transmission electron micrographs of FACS-purified D0 (Top), and D112 (Bottom) EGFP$^+$ spermatogonia displaying properties of undifferentiated type A spermatogonia. Images are magnified ~4000×. (C) DNA content of FACS-purified, EGFP$^+$ spermatogonia after 120 days of culture in SA medium (Top) and of freshly isolated testes cells from 17 (Middle) and 45 (Bottom) day old rats. DNA content values are expressed as 1C, 2C and 4C for haploid, diploid and tetraploid populations, respectively.

The germ cells were passaged 12 times while in SA-medium, spanning 151 days of culture, and the numbers of germ cells were expanded by ~20,000-fold relative to the initial cell number (FIG. 9C). Thus, from 200,000 freshly isolated $Lam_B$ germ cells, approximately 4 billion EGFP$^+$ germ cells have been generated. After 110-140 days in culture, the EGFP$^+$ cells remained positive for DAZL (FIG. 10A), maintained a normal number of rat chromosomes (42/cell), and are type A spermatogonia based on both morphology (FIG. 10B) and DNA content (FIG. 10C).

Figure 11:
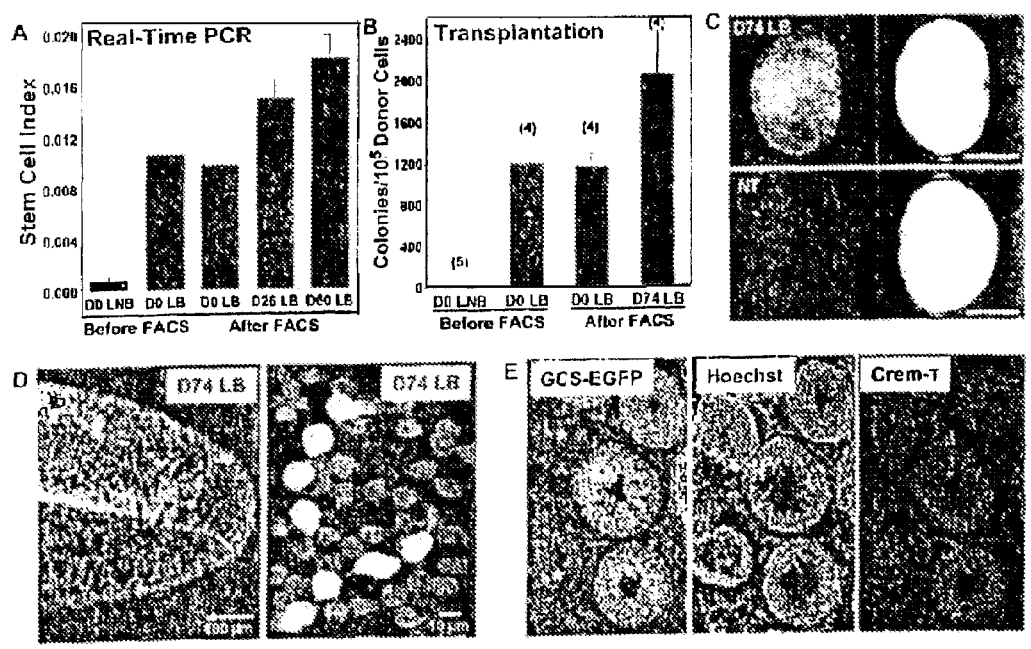
FIG. 11 illustrates the stem cell activity of EGFP$^+$ spermatogonia. (A) Stem cell index (SSCI) values for GCS-EGFP$^+$ Lam$_B$ germ cells (D0 LB) before and after (D0, D26 and D60 LB) purification from somatic cells by FACS. After FACS, EGFP$^+$ cells were analyzed directly (D0 LB) or plated onto MEFs. After 26 and 60 days on MEFs (D26 and D60 LB), EGFP$^+$ cells were purified again by FACS and their SSCI values were determined. SSCI values are also shown for D0 GCS-EGFP$^+$ Lam$_{NB}$ germ cells (D0 LNB). (B) The number of EGFP$^+$ colonies formed/testis by donor GCS-EGFP$^+$ germ cells. One thousand EGFP$^+$ germ cells were transplanted/testis before (D0 LNB, D0 LB) or after (D0 and D74 LB) their purification by FACS. Purified germ cells were maintained on MEFs for 0 (D0) or 74 days (D74) prior to transplantation. Parentheses contain the number of testes and recipient rats analyzed. (C) (top left, D74 LB) Right testis from a WT rat transplanted 63 days earlier with ~10$^5$ D74 EGFP$^+$ spermatogonia. (top right) Bright field image of the same testis. (bottom left and right) Respective images of the non-transplanted (NT), left testis from the same rat. Note green fluorescence only in the transplanted testis. Scale bar, 5 mm. (D) (left) Seminiferous tubule from a WT recipient rat containing an EGFP$^+$ colony derived from D74 EGFP$^+$ spermatogonia. (right) Higher magnification of the same colony. (E) (left) Cross section through the transplanted testis in top of panel C showing seminiferous tubules colonized by D74 EGFP+ spermatogonia (green). (Center) Nuclei of cells in the same section stained with Hoechst 33342 (blue). (Right) The same section showing donor cells that have developed into round spermatids (Crem-τ, red). Asterisks denote tubules of the WT recipient that were not colonized by donor cells.
Figure 13:
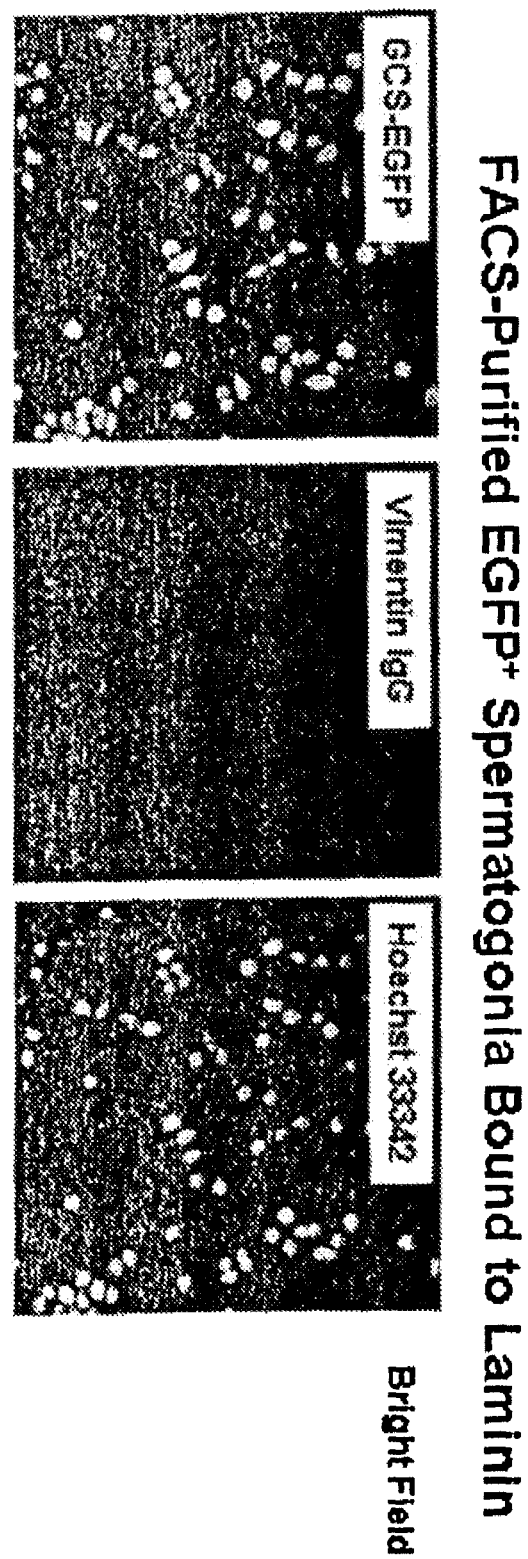
FIG. 13 shows that proliferating cultures of GCS-EGFP+ spermatogonia bind to laminin, but not collagen. GCS-EGFP+ spermatogonia were purified by FACS (see FIG. 12) after 127 days in culture and then plated into collagen-I-coated culture dishes in SB medium. After 4 hr at 37° C., 5% $CO_2$ the germ cells remained unbound to collagen and were then placed on laminin-coated culture dishes in SB medium. Essentially all germ cells were bound to laminin after 45 min in culture at 37° C., 5% $CO_2$ Images of GCS-EGFP+, vimentin− cultures are shown binding to laminin after fixation. Immunocytochemical labeling was with Cy3-conjugated, anti-vimentin IgG and Hoechst 33342.

The marker transcripts associated with spermatogonial stem cell activity described above are ~2-fold more abundant in the 74 day-old EGFP$^+$ spermatogonial cultures than in D0 $Lam_B$ spermatogonia (FIG. 11A). Transplantation of the D74 EGFP$^+$ spermatogonia to the testes of busulfan-treated rats showed no loss in stem cell activity (FIG. 11BCD). Additionally, the EGFP$^+$ spermatogonia from these cultures developed into spermatids (EGFP$^+$, Crem tau$^+$) within 62 days after transplantation to recipient rat testes (FIG. 11E). Testicular tumors were not observed after transplantation (n=15 testes transplanted with a total of ~3×10$^5$ EGFP$^+$ cells). Also, as with D0 $Lam_B$ spermatogonia, the EGFP$^+$ cells grown in these cultures bound avidly to laminin but not collagen (FIG. 13).

Figure 14:
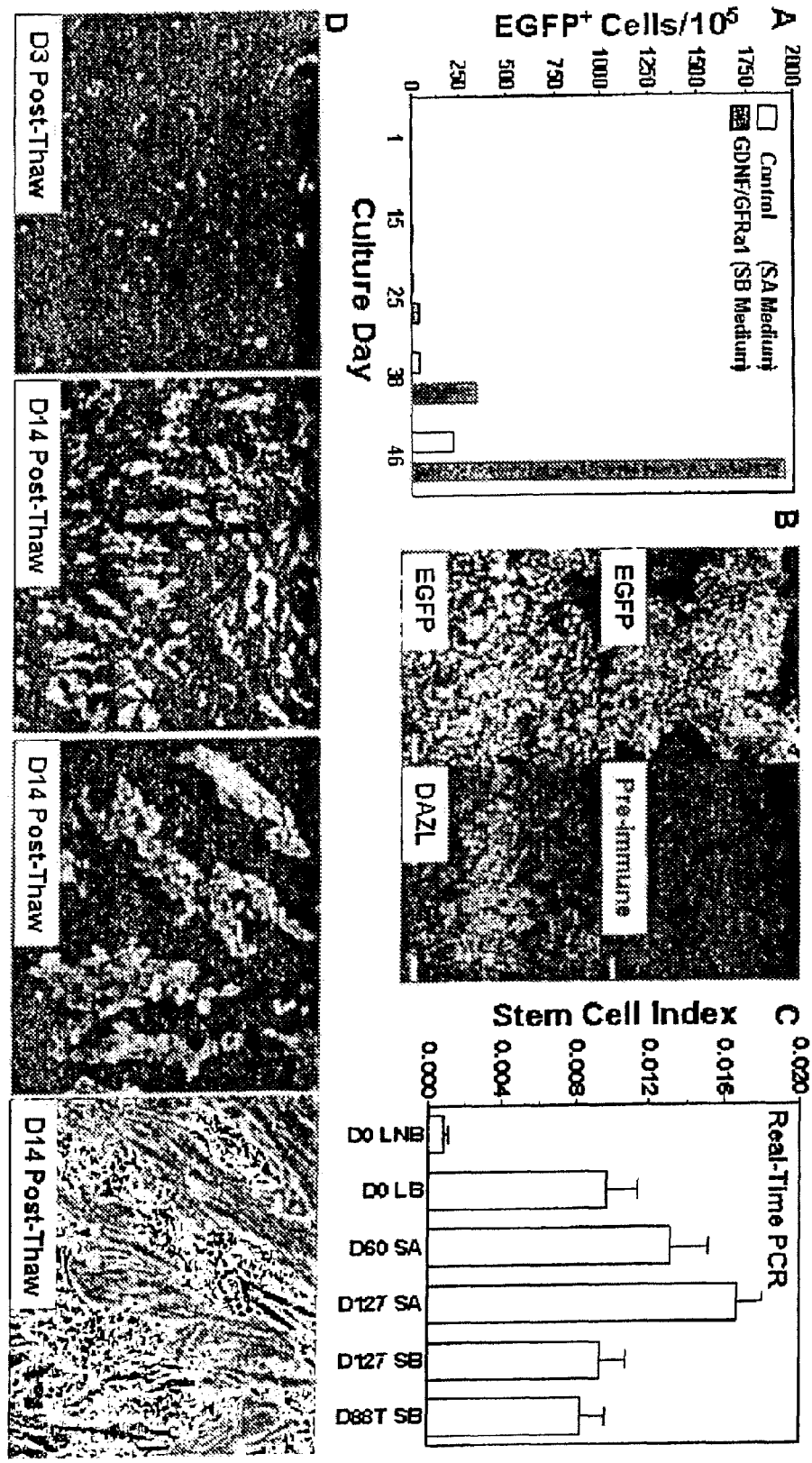
FIG. 14 illustrates the propagation of EGFP+ spermatogonia after cyropreservation. (A) Effect of GFRα1 and GDNF on proliferation of EGFP+ spermatogonia. After 6 passages in SA medium, EGFP+ spermatogonia were passed and propagated in SA medium with increased concentrations of GDNF (45 ng/ml) and GFRα1 (285 ng/ml) (SB medium) to the indicated days. (B) Expression of the germ cell marker protein DAZL (red) in EGFP+ spermatogonia after 26 days (3-passages) in SB media. (C) SSCI values for D0 $Lam_B$ (D0 LB) and $Lam_{NB}$ (D0 LNB) germ cells, $Lam_B$ germ cells propagated for up to 127 days (D60, D127) in either SA medium (SA), or SB medium (SB); or in SB medium following one month storage in liquid nitrogen and subsequent thawing and culture for 14 days (D88T). (D) Propagation of EGFP+ spermatogonia in SB medium after one month storage in liquid nitrogen (cryopreserved 34 days in SA medium containing 10% DMSO). (left, D3 Post-Thaw) Day 3 culture after thawing. (left-center, D14 Post-Thaw) Thawed cells that had been cultured for one week on MEFs, trypsinized, passed at a 1:2 dilution and then expanded for 7 more days on new MEFs. (right-center and right) Higher magnification fluorescence and phase contrast images of cells shown in the left-center panel.

Addition of GFRα1 and/or bFGF to a serum-free medium that contained GDNF is preferable for expansion of mouse spermatogonial stem cells in a C57B1/6 background (Ref. 39). When the concentrations of GDNF and GFRα1 were increased in SA-medium (SB-medium), even more robust expansion of EGFP$^+$ rat germ cells occurred (FIG. 14). Under these conditions the EGFP$^+$ population doubled at least once every 3.5 days (FIG. 14A), remained positive for DAZL (FIG. 14B), and maintained their SSCI values (FIG. 14C). Initial SSCI values for EGFP$^+$ spermatogonia were also maintained after one month of storage in liquid nitrogen, subsequent thawing and culture in SB medium (FIG. 14CD).

EXAMPLE 7

Ttransfection of Spermatogonia

A. Generation of DNA Constructs.

The human ubiquitin (UB) promoter was isolated from pUB6/V5-His (Invitrogen, Inc.) using BglII and BamHI and then ligated into the BamHI site of pDsRed2-1 (BD Biosciences, Inc.) to generate pUB-DsRed2-1. The coding sequence of EGFP was isolated from pcDNA6.0-EGFP-V5-His-B (Ref. 24) using HindIII and XhoI and then ligated into the HindIII and XhoI sites of pUB6/V5-His to generate pUB-EGFP. The rat olfactory marker protein gene targeting vector (pOMP-TV2-1) was generated by amplifying a 5.2 kb (5' homology arm) and 3.2 kb (3' homology arm) by PCR (KOD Polymerase, Novagen, Inc.) from genomic DNA isolated from tail snips of GCS-EGFP rats that were determined to be isogenic for the target OMP locus. Primers were designed based on a BAC clone sequence containing the entire OMP gene identified in the rat genome database and correspond to base pairs 14276711-14281923 (5' homology arm) and 14268243-14271482 (3' homology arm) in the current contig of rat chromosome 1 (NW_047561, Build 3.1). The PCR products containing both homology arms were ligated into pCR-XL-TOPO (Invitrogen, Inc.) to generate pCR-XL-OMP-LA and pCR-XL-OMP-SA. A 5.2 kb, 5' arm was isolated from pCR-XL-TOPO-LA using KpnI and HindIII and ligated into KpnI and HindIII sites within pKO scrambler NTKV-1904 (Stratagene, Inc.) to generate pOMP-TV-LA. A 2.15 kb, 3' arm was isolated from pCR-XL-TOPO-SA using BamHI and XhoI and then ligated into BglII and XhoI sites within pKO scrambler 1904 NTKV to generate pOMP-TV-2-1. A mock OMP chromosome plasmid was generated to establish a PCR assay for identifying correctly targeted mutations of in the OMP gene by isolating the full length 3.2 kb, 3' homology arm from pCR-XL-TOPO-SA using EcoRI, which was then ligated into the EcoRI site of pOMP-TV-LA to generate pOMP-M.

B. Transfection of Spermatogonia.

Day 0 WT or GCS-EGFP $Lam_B$ spermatogonia, or cultures of expanding populations of GCS-EGFP$^+$ spermatogonia were suspended to ~1.25×10$^6$ cells/ml in their respective culture medium. The transfection mixture containing Lipofectamine 2000 (Invitrogen, Inc.) and plasmid DNA was prepared in Opti-MEM-I (Invitrogen, Inc.) according to the manufacturer's protocol. The mixture (Lipofectamine:DNA=1 µl:0.5 µg in 100 µl Opti-MEM-I) was added to the cell suspension (20% vol mix:80% vol cell suspension) and incubated (37° C., 5% $CO_2$) for 40 to 120 min (routinely 80 min). During transfections lasting longer than 1 hr the cells were re-suspended by gently pipetting them up and down two times midway through the incubation period. Following the incubation period, the cells were washed by suspending them to 10 times the initial volume with fresh culture medium, and then were pelleted for 5 min at 500×g. The supernatant fluid was discarded and the pellets were washed 2 additional times. After the third wash, the cell pellets were suspended in fresh medium from their respective culture conditions and then plated on fresh fibroblast feeder layers. Before transfecting the EGFP$^+$ spermatogonia by this method, they were passaged onto gelatin-coated plates for a 30 min period to reduce the number of feeder cells present in the transfection.

Figure 12:
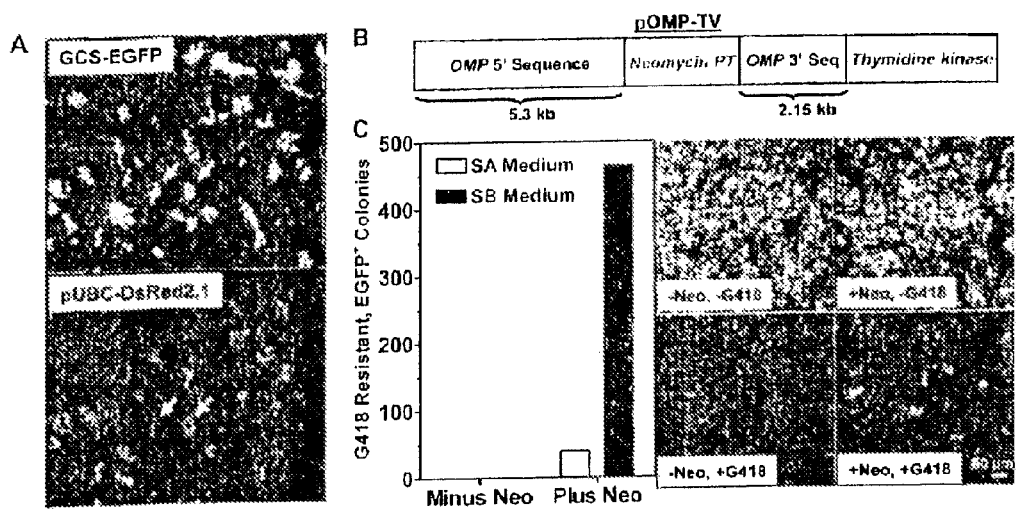
FIG. 12 illustrates the transfection of rat spermatogonia. (A) GCS-EGFP+-spermatogonia (top, green) that were transfected with pUBC-DsRed2.1 (bottom, red) for 80 minutes. Greater than 20% of the EGFP+ spermatogonia were transfected based on counting red-fluorescent cells on a hemocytometer. (B) Diagram of OMP gene replacement vector (pOMP-TV). (C) (left) Number of G418 resistant, EGFP+ colonies obtained after transfecting rat EGFP+ spermatogonia with pOMP-TV and selection in 200 µg/ml (SA medium) and 150 µg/ml (SB medium) G418. (right) Images of EGFP+ spermatogonia either mock-transfected without DNA (−Neo), or transfected with pOMP-TV (+Neo) after selection without (−G418) or with (+G418) 150 µg/ml G418 in SB medium. Colonies were scored and images were taken at day 14 post-transfection and after 10 days of selection in G418-containing medium.
Figure 15:
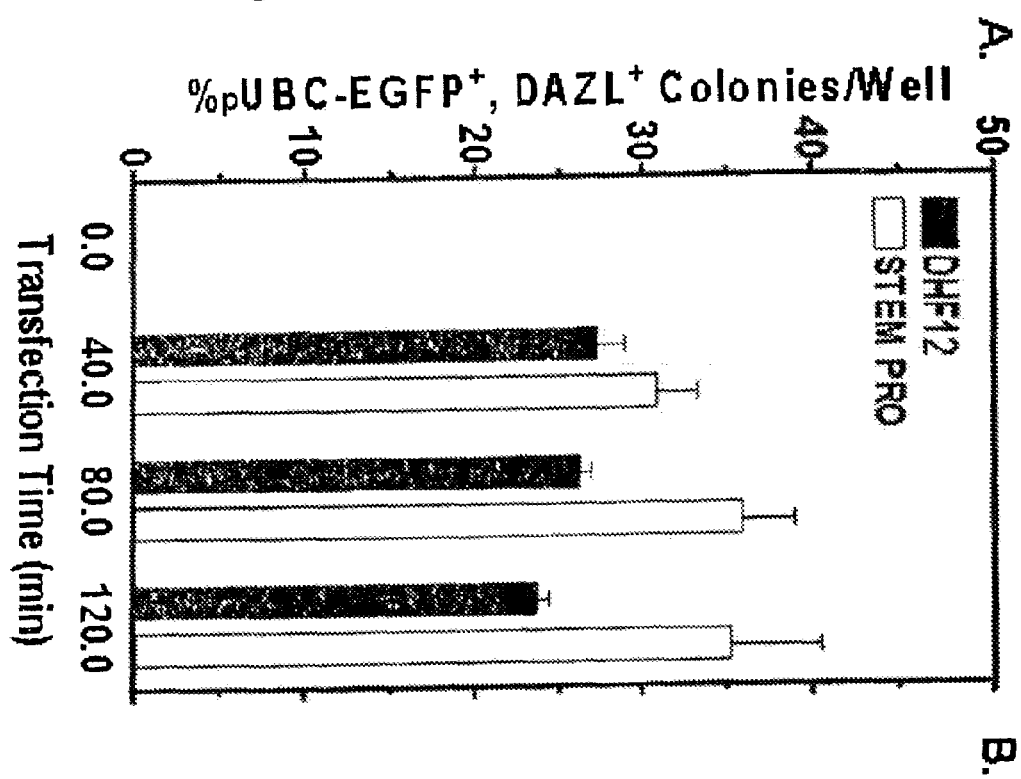
FIG. 15 illustrates the transfection of freshly isolated WT rat $Lam_B$ spermatogonia. (A) Percentage of DAZL+ WT spermatogonia transfected with a plasmid DNA reporter construct expressing EGFP under control of the human ubiquitin C promoter (pUBC-EGFP). Freshly isolated $Lam_B$ spermatogonia were transfected in suspension using Lipofectamine 2000 reagent (Invitrogen, Inc.) for the indicated times. (B) A colony of DAZL+ (Top, red), pUBC-EGFP+ (Bottom, green) germ cells that developed after 8 days in culture on mouse embryonic fibroblasts after transfection of WT D0 $Lam_B$ spermatogonia for 40 min. Note the adjacent DAZL+ germ cell colony from the same transfection reaction does not appear to express the pUBC-EGFP reporter.
Figure 15:
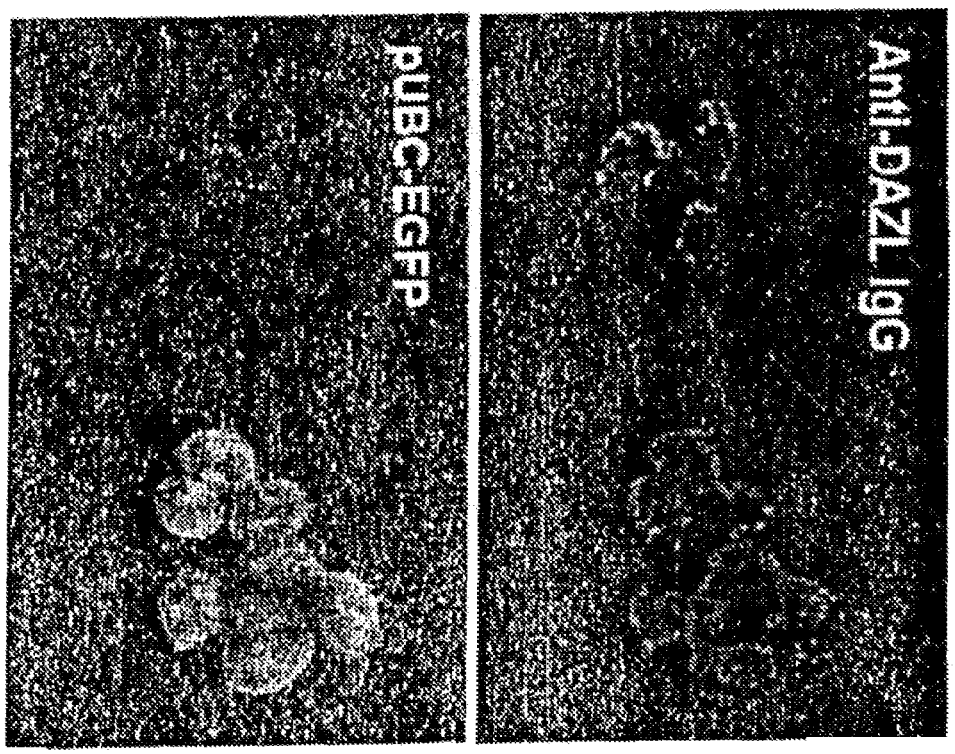

Conditions for transfecting WT D0 $Lam_B$ spermatogonia with Lipofectamine 2000 were optimized, using a DNA reporter plasmid encoding EGFP (pUBC-EGFP) by lipofection (FIG. 15), and then applied these methods to expanding cultures of EGFP$^+$ spermatogonia (FIG. 12A). As with WT spermatogonia, >20% of the EGFP$^+$ spermatogonia cultured in SB medium were transfected with pUBC-DsRed2.1, which encodes a red-fluorescent marker protein. (FIG. 12A).

Following the initial success using lentiviral constructs to transduce D0 rat $Lam_B$ spermatogonial stem cells in culture (Ref. 25), a gene replacement construct was generated to modify rat spermatogonial stem cells at a desired genomic locus by homologous recombination. The targeting construct generated, pOMP-TV (FIG. 12B), contains a total of 7.35 kilo-base pairs (kb) of rat genomic sequence from chromosome 1q32, that includes a 5.2 kb, 5' arm and a 2.15 kb, 3' arm, which flank the open reading frame of the rat gene, olfactory marker protein (Omp). The construct also contains a positive selection cassette (neo) inserted between the 5' and 3' arms, and a negative selection cassette (thymidine kinase) positioned directly outside the 3' arm (FIG. 12B). These markers are also commonly used to select for mouse ES cells with targeted genomic modifications (Ref. 40). Because isogenic DNA increases the rate of homologous recombination in mouse lines by 10-100 times (Ref. 41), a colony of GCS-EGFP rats that are isogenic for the Sprague Dawley Omp allele used in the Omp targeting construct was generated.

The rat Omp targeting construct was transfected into EGFP$^+$ spermatogonia and selection was initiated with G418. After 10 days, more than 20 G418-resistant colonies were selected/10$^5$ transfected EGFP$^+$ cells when cultured in SA medium, whereas under separate conditions, ~580 G418-resistant colonies were selected/10$^5$ transfected EGFP$^+$ cells after 10 days in SB medium (FIG. 12C). Under conditions of mock transfection for either condition, no EGFP$^+$ colonies survived the selection protocol (FIG. 12C). In recipient rats, the G418-resistant germ cells generated 1130±550 (±SEM, n=4) GCS-EGFP$^+$ colonies/testis/10$^5$ donor cells.

REFERENCES

Each of the following references and any other reference cited is incorporated herein in its entirety.

1. Chiquoine, A. D. (1954). The identification, origin, and migration of the primordial germ cells in the mouse embryo. Anat Rec 118, 135-46.
2. Ginsburg, M., Snow, M. H., and McLaren, A. (1990). Primordial germ cells in the mouse embryo during gastrulation. Development 110, 521-8.
3. Okazawa, H., Okamoto, K., Ishino, F., Ishino-Kaneko, T., Takeda, S., Toyoda, Y., Muramatsu, M., and Hamada, H. (1991). The oct3 gene, a gene for an embryonic transcription factor, is controlled by a retinoic acid repressible enhancer. Embo J 10, 2997-3005.
4. Yoshimizu, T., Sugiyama, N., De Felice, M., Yeom, Y. I., Ohbo, K., Masuko, K., Obinata, M., Abe, K., Scholer, H. R., and Matsui, Y. (1999). Germline-specific expression of the Oct-4/green fluorescent protein (GFP) transgene in mice. Dev Growth Differ 41, 675-84.
5. Fox, N., Damjanov, I., Martinez-Hernandez, A., Knowles, B. B., and Solter, D. (1981). Immunohistochemical localization of the early embryonic antigen (SSEA-1) in postimplantation mouse embryos and fetal and adult tissues. Dev Biol 83, 391-8.
6. Lange, U. C., Saitou, M., Western, P. S., Barton, S. C., and Surani, M. A. (2003). The fragilis interferon-inducible gene family of transmembrane proteins is associated with germ cell specification in mice. BMC Dev Biol 3, 1.
7. Chambers, I., Colby, D., Robertson, M., Nichols, J., Lee, S., Tweedie, S., and Smith, A. (2003). Functional expression cloning of Nanog, a pluripotency sustaining factor in embryonic stem cells. Cell 113, 643-55.
8. Tsuda, M., Sasaoka, Y., Kiso, M., Abe, K., Haraguchi, S., Kobayashi, S., and Saga, Y. (2003). Conserved role of nanos proteins in germ cell development. Science 301, 1239-41.
9. Tanaka, S. S., Toyooka, Y., Akasu, R., Katoh-Fukui, Y., Nakahara, Y., Suzuki, R., Yokoyama, M., and Noce, T. (2000). The mouse homolog of Drosophila Vasa is required for the development of male germ cells. Genes Dev 14, 841-53.
10. Enders, G. C., and May, J. J., 2nd. (1994). Developmentally regulated expression of a mouse germ cell nuclear antigen examined from embryonic day 11 to adult in male and female mice. Dev Biol 163, 331-40.
11. Gill, T. J., 3rd, Smith, G. J., Wissler, R. W. & Kunz, H. W. (1989) Science 245, 269-76.
12. Hedrich, H. (2000) History Strains and Models of The Laboratory Rat (Academic Press, San Diego.
13. Abbott, A. (2004) Nature 428, 464-6.
14. Zambrowicz, B. P., Imamoto, A., Fiering, S., Herzenberg, L. A., Kerr, W. G., and Soriano, P. (1997). Disruption of overlapping transcripts in the ROSA beta geo 26 gene trap strain leads to widespread expression of beta-galactosidase in mouse embryos and hematopoietic cells. Proc Natl Acad Sci USA 94, 3789-94.
15. Kisseberth, W. C., Brettingen, N. T., Lohse, J. K., and Sandgren, E. P. (1999). Ubiquitous expression of marker transgenes in mice and rats. Dev Biol 214, 128-38.
16. Young, S., Aldons, J L., Hammer, R E. (1999). Molecular Basis of Cardiovascular Disease. In "Genetically Modified Animal Models in Cardiovascular Research" (K. Chien, Ed.), pp. 37-85. W. B. Saunders Company, Philadelphia.
17. MacLean-Hunter, S., Evans, M. (1999). Non-Surgical Method for the Indution of Delayed Implantation and Recovery of Viable Blastoysts in Rats and Mice by the Use of Tamoxifen and Depo-Provera. Molecular Reproduction and Development 52, 29-32.
18. Hogan, B., Beddington, R, Costantini, F, and Lacy, E. (1994). "Manipulating the mouse embryo: A laboratory manual." Cold Spring Harbor Laboratory Press, Plainview, N.Y.
19. Islam, M. Q., and Levan, G. (1987). A new fixation procedure for quality G-bands in routine cytogenetic work. Hereditas 107, 127-30.
20. Behboudi, A., Roshani, L., Kost-Alimova, M., Sjostrand, E., Montelius-Alatalo, K., Rohme, D., Klinga-Levan, K., and Stahl, F. (2002). Detailed chromosomal and radiation hybrid mapping in the proximal part of rat Chromosome 10 and gene order comparison with mouse and human. Mamm Genome 13, 302-9.
21. Helou, K., Yan, Q., Yuan, X. J., Kunz, H. W., Levan, G., and Gill, T. J., 3rd. (1999). Cytogenetic localization of the growth and reproduction complex (Grc) in the rat and in the mouse and its position in relation to RT1.EC and other loci in the rat MHC. Hereditas 130, 105-9.
22. Palmiter, R. D., and Brinster, R. L. (1986). Germ-line transformation of mice. Annu Rev Genet 20, 465-99.
23. Zernicka-Goetz, M. (1994). Activation of embryonic genes during preimplantation rat development. Mol Reprod Dev 38, 30-35.

24. Hamra, F., Schultz, N., Chapman, K. M., Grellhesl, D. M., Cronkhite, J. T., Hammer, R. E., and Garbers, D. L. (2004). Defining the spermatogonial stem cell. Dev Biol 269, 393-410.
25. Hamra, F. K., Gatlin, J., Chapman, K. M., Grellhesl, D. M., Garcia, J. V., Hammer, R. E., and Garbers, D. L. (2002). Production of transgenic rats by lentiviral transduction of male germ-line stem cells. Proc Natl Acad Sci USA 99, 14931-6.
26. Ogawa, T., Arechaga, J. M., Avarbock, M. R., and Brinster, R. L. (1997). Transplantation of testis germinal cells into mouse seminiferous tubules. Int J Dev Biol 41, 111-22.
27. Brinster, R. L., and Zimmermann, J. W. (1994). Spermatogenesis following male germ-cell transplantation. Proc Natl Acad Sci USA 91, 11298-302.
28. Dobrinski, I., Avarbock, M. R., and Brinster, R. L. (2000). Germ cell transplantation from large domestic animals into mouse testes. Mol Reprod Dev 57, 270-9.
29. Nagano, M., and Brinster, R. L. (1998). Spermatogonial transplantation and reconstitution of donor cell spermatogenesis in recipient mice. Apmis 106, 47-55; discussion 56-7.
30. Schultz, N., Hamra, F. K. & Garbers, D. L. (2003) Proc Natl Acad Sci USA 100, 12201-6.
31. Heid, C. A., Stevens, J., Livak, K. J. & Williams, P. M. (1996) Genome Res 6, 986-94.
32. Gibson, U. E., Heid, C. A. & Williams, P. M. (1996) Genome Res 6, 995-1001.
33. Mather, J. P., Saez, J. M. & Haour, F. (1981) Steroids 38, 35-44.
34. Kanatsu-Shinohara, M., Ogonuki, N., Inoue, K., Miki, H., Ogura, A., Toyokuni, S. & Shinohara, T. (2003) Biol Reprod 69, 612-6.
35. Ogawa, T., Dobrinski, I. & Brinster, R. L. (1999) Tissue Cell 31, 461-72.
36. McMahon, A. P. & Bradley, A. (1990) Cell 62, 1073-85.
37. McGuinness, M. P., Linder, C. C., Morales, C. R., Heckert, L. L., Pikus, J. & Griswold, M. D. (1994) Biol Reprod 51, 116-24.
38. Malkov, M., Fisher, Y. & Don, J. (1998) Biol Reprod 59, 84-92.
39. Kubota, H., Avarbock, M. R. & Brinster, R. L. (2004) Proc Natl Acad Sci USA 101, 16489-94.
40. Cheah, S. S. & Behringer, R. R. (2001) Mol Biotechnol 19, 297-304.
41. te Riele, H., Maandag, E. R. & Berns, A. (1992) Proc Natl Acad Sci USA 89, 5128-32.

What is claimed is:

1. A rat spermatogonial stem cell line comprising cells deposited as ATTC accession No. PTA-7214 that expresses EGFP.

2. A cell culture comprising the cell line of claim 1 and culture medium that is free of serum and vitamin A but contains GDNF family receptor α1.

3. A transgenic rat produced from the rat spermatogonial stem cell line of claim 1, wherein the rat expresses EGFP exclusively in the germ line.

4. The transgenic rat of claim 3, wherein said rat is a female rat that expresses EGFP exclusively in egg cells.

* * * * *